(12) United States Patent
Hickey et al.

(10) Patent No.: US 6,971,383 B2
(45) Date of Patent: Dec. 6, 2005

(54) DRY POWDER INHALER DEVICES, MULTI-DOSE DRY POWDER DRUG PACKAGES, CONTROL SYSTEMS, AND ASSOCIATED METHODS

(75) Inventors: Anthony J. Hickey, Chapel Hill, NC (US); Timothy M. Crowder, Chapel Hill, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 230 days.

(21) Appl. No.: 10/204,609

(22) PCT Filed: Jan. 24, 2001

(86) PCT No.: PCT/US01/02262

§ 371 (c)(1),
(2), (4) Date: Jan. 29, 2003

(87) PCT Pub. No.: WO01/68169

PCT Pub. Date: Sep. 20, 2001

(65) Prior Publication Data

US 2004/0123864 A1 Jul. 1, 2004

(51) Int. Cl.[7] ............................................. A61M 15/00
(52) U.S. Cl. ........................... 128/203.15; 128/203.12; 604/58
(58) Field of Search ....................... 128/203.15, 203.12, 128/203.21, 200.16, 200.14; 239/102.1, 102.2; 604/58

(56) References Cited

U.S. PATENT DOCUMENTS

| | | | |
|---|---|---|---|
| 3,565,070 A | 2/1971 | Hanson et al. | 128/173 |
| 3,948,284 A | 4/1976 | Walworth | 138/238 |
| 4,472,091 A | 9/1984 | Callahan | |
| 4,607,254 A | 8/1986 | Carlson | 340/606 |
| 4,819,620 A | 4/1989 | Okutsu | 128/4 |
| 5,261,601 A | 11/1993 | Ross et al. | |
| 5,388,572 A | 2/1995 | Mulhauser et al. | |
| 5,619,984 A | 4/1997 | Hodson et al. | |
| 5,622,166 A | 4/1997 | Eisele et al. | |
| 5,655,523 A | 8/1997 | Hodson et al. | |
| 5,694,920 A | 12/1997 | Abrams et al. | 128/200.16 |
| 5,740,793 A | 4/1998 | Hodson et al. | |
| 5,743,250 A | 4/1998 | Gonda et al. | |
| 5,826,570 A | 10/1998 | Goodman et al. | |
| 5,829,436 A | 11/1998 | Rubsamen et al. | |
| 5,857,456 A | 1/1999 | Sun et al. | |
| D410,541 S | 6/1999 | Moulin | D24/110 |
| 6,012,454 A | 1/2000 | Hodson et al. | |
| 6,026,809 A | 2/2000 | Abrams et al. | |
| 6,063,138 A | 5/2000 | Hanna et al. | 23/295 |
| 6,095,142 A | 8/2000 | Giorgini | 128/205 |

(Continued)

FOREIGN PATENT DOCUMENTS

CH         0923957 A1     6/1999

(Continued)

Primary Examiner—Mital Patel
(74) Attorney, Agent, or Firm—Jenkins, Wilson & Taylor, P.A.

(57) ABSTRACT

Dry powder inhalers (FIG. 1) with integrated active energy patient assist dispersal systems are configured with control systems which provide adjustable energy output responsive to the user's inspiratory capabilities and/or the flowability of the dry powder being administered. The multi-dose dry drug package (FIG. 2) a piezoelectric polymer substrate which flexes to deform and provide mechanical oscillation in a selected region of the package corresponding to the dry powder drug which is dispersed during inhalation by a user. Control system (FIG. 12) employs fuzzy logic to relate in response to a user's inspiratory effort.

33 Claims, 14 Drawing Sheets

U.S. PATENT DOCUMENTS

| | | | |
|---|---|---|---|
| 6,142,146 A | 11/2000 | Abrams et al. | 128/203.15 |
| 6,143,277 A | 11/2000 | Ashurst et al. | 424/45 |
| 6,152,130 A | 11/2000 | Abrams et al. | 128/204.21 |
| 6,192,876 B1 | 2/2001 | Denyer et al. | 125/205.25 |
| 6,196,298 B1 | 3/2001 | Shaw | |
| 6,288,360 B1 | 9/2001 | Beste | 219/121.71 |
| 6,295,986 B1 | 10/2001 | Patel et al. | 128/203.12 |
| 6,328,033 B1 * | 12/2001 | Avrahami | 128/203.15 |
| 6,351,984 B1 | 3/2002 | Srinivasan | 73/40.7 |
| 6,354,516 B1 | 3/2002 | Patel et al. | 239/331 |
| 6,369,354 B1 | 4/2002 | Beste | 219/121.71 |

FOREIGN PATENT DOCUMENTS

| | | |
|---|---|---|
| EP | 0 129 985 | 1/1985 |
| EP | 1 106 196 A2 | 6/2001 |
| EP | 1 166 812 A1 | 1/2002 |
| EP | 1 172 122 | 1/2002 |
| WO | 01/68169 A1 | 9/2001 |

* cited by examiner

DRY POWDER INHALER DEVICES, MULTI-DOSE DRY POWDER DRUG PACKAGES, CONTROL SYSTEMS, AND ASSOCIATED METHODS

FIELD OF THE INVENTION

The present invention relates generally to drug delivery devices and more particularly to dose-regulated dry powder inhalers.

BACKGROUND OF THE INVENTION

Delivery of drugs as inhaled aerosols is well known. Indeed, asthma and other respiratory ailments have long been treated with inhaled aerosols. Presently, there is also an interest in expanding this administration concept to locally acting agents such as antimicrobials, protease inhibitors, and nucleic acids/oligios as well as systemic agents such as peptides like leuprolide and proteins such as insulin. For example, inhaler based delivery of antimicrobial agents such as antitubercular compounds, proteins such as insulin for diabetes therapy or other insulin-resistant related disorders, peptides such as leuprolide acetate for treatment of prostate cancer and endometriosis and nucleic acids or ogligonucleotides for cystic fibrosis gene therapy. See e.g. Wolff et al., *Generation of Aerosolized Drugs*, J. Aerosol: Med. pp. 89–106 (1994).

Generally described, there are three types of inhaler devices used to administer and deliver drug therapies via aerosol-based inhalation. The most common type used (typically associated with asthma treatments) is the pressurized metered dose inhaler (pMDI). This type of inhaler uses an ozone-depleting CFC propellant such as freon, which is banned for most commercial applications, but which presently has medical exemption. Alternatives to the pMDI devices are an important area of aerosol delivery research primarily because the number of non-CFC propellants is limited and reformulation is difficult.

Inhalant drug aerosols can also be generated by the use of nebulizers. Until recently, use of these nebulizer-type devices was typically limited to clinical sites and the home due primarily to their power requirements. In operation, nebulizers deliver droplets in a size range that enables the drug to reach the periphery of the lung through the air passage of a patient. However, because the droplets are very small (such as on the order of less than about 2.0 $\mu$m), a relatively long treatment time is usually required to deliver a clinically significant dose.

A third type of inhaler is a dry powder inhaler (DPI), which represents a promising alternative to pMDI devices for delivering drug aerosols. Typically, the DPIs are configures to deliver a powdered drug or drug mixture which includes an excipient and/or other ingredients. Conventionally, many DPIs have operated passively, relying on the inspiratory effort of the patient to dispense the drug provided by the powder. Unfortunately, this passive operation can lead to poor dosing uniformity since inspiratory capabilities can vary from patient to patient (and sometimes even use to use by the same patient, particularly if the patient is undergoing an asthmatic attack or respiratory-type ailment which tends to close the airway).

Generally described, known single and multiple dose dry powder DPI devices use either individual pre-measured doses, such as capsules containing the drug, which can be inserted into the device prior to dispensing. Alternatively, DPI devices can operate based on bulk powder reservoirs which are configured to administer successive quantities of the drug to the patient via a dispensing chamber which dispenses the proper dose. See generally Prime et al., *Review of Dry Powder Inhalers*, 26 Adv. Drug Delivery Rev., pp. 51–58 (1997); and Hickey et al., *A new millennium for inhaler technology*, 21 Pharm. Tech., n. 6, pp. 116–125 (1997).

In operation, particularly of DPI devices, it is desired that a uniform dispersion amount and desired physical form (such as a particulate size) of the dry powder be dispersed into a patient's airway and directed to the desired deposit site. If the patient is unable to provide sufficient respiratory effort, the extent of drug penetration, especially to the lower portion of the airway, may be impeded. This may result in premature deposit of the powder in the patient's mouth or throat.

Further, a number of obstacles can desirably affect the performance of the DPI. For example, the small size of the inhalable particles in the dry powder drug mixture can subject them to forces of agglomeration and/or cohesion (i.e., certain types of dry powders are susceptible to agglomeration, which is typically caused by particles of the drug adhering together), which disadvantageously results in poor flow and non-uniform dispersion. In addition, as noted above, many dry powder formulations employ larger excipient particles to promote flow properties of the drug. However, separation of the drug from the excipient as well as the presence of agglomeration can require additional inspiratory effort, which again, can impact the stable dispersion of the powder within the airstream of the patient such that it reaches its preferred deposit/destination site and reduces the amount of the drug which is prematurely deposited elsewhere.

Further, many dry powder inhalers can retain a significant amount of the drug within the device, which can be especially problematic over time. Typically, this problem requires that the device be cleansed to assure that it is in proper working order. In addition, the hygroscopic nature of many of these dry powder drugs may also require that the device be cleansed (and dried) at periodic intervals.

Some inhalation devices have attempted to resolve problems attendant with conventional passive inhalers. For example, U.S. Pat. No. 5,655,523 proposes a dry powder inhalation device which has a deagglormeration/aerosolization plunger rod or biased hammer and solenoid and U.S. Pat. No. 3,948,264 proposes the use of a battery-powered solenoid buzzer to vibrate the capsule to effectuate the release of the powder contained therein. These devices propose to facilitate the release of the dry powder by the use of energy input independent of patient respiratory effort. However, there remains a need to provide improved, easy to use, cost effective, and reliable dry powder inhalers.

OBJECTS AND SUMMARY OF THE INVENTION

It is therefore an object of the present invention to provide an improved dry powder inhaler which can disperse more uniform doses.

It is another object of the present invention to provide a DPI system to actively facilitate the dispersion and release of dry powder drug formulations during inhalation which can increase the quantity of fine particle fraction particles dispersed or emitted from the device over convention DPI systems.

It is another object of the present invention to provide an economic, disposable blister package configuration with active dispersion elements and multiple dry powder doses positioned thereon to reduce the cleaning difficulty and frequency of the inhaler.

It is an additional object of the present invention to provide an integrated control system for an inhaler that can adjust the operation of the inhaler based on actively detected or predetermined parameters.

It is yet another object of the present invention to provide control systems which are configured to analyze predetermined conditions and/or parameters which can dynamically adjust the operation of the inhaler during use.

It is a further object of the present invention to provide logic-based control systems to determine and adjust the operation of devices and/or apparatus that employ and/or dispense dry powder substances.

These and other objects of the present invention are provided by methods, systems, and computer program products for administering and dispensing dry powder based drug formulations via inhalers. Preferably, a multi-layer active drug package is configured to vibrate or oscillate in response to the application of an excitation voltage thereto. The multi-layer drug package is preferably a drug blister package configured to protect the drug from humidity prior to active dispersion of the dose. The multi-layer drug blister package employs a thin layer of piezoelectric polymer material such as polyvinylidene fluoride ("PVDF") film with electrical traces configured thereon to apply the electrical excitation voltage differential thereacross at the desired region of the package and oscillate the drug package about the drug blister region to actively assist and disperse the dry powder dose into the air stream of a user during the inspiratory use. In addition, the inhaler can use a fuzzy logic based control system and one or more sensors to provide active control/feedback and dynamic adjustments to the dispersion control system based on sensed real-time conditions (such as user air flow rate, temperature, humidity and the like) and/or predetermined conditions and parameters corresponding to the drug being delivered or the systemic target of same.

As will be appreciated by those of skill in the art, the present invention may be provided as one or combinations of devices, methods, systems, or computer program products.

A first aspect of the present invention is directed to a multi-dose dry powder blister package. The package includes a platform body comprising a piezoelectric material layer with opposing first and second major surfaces. The first major surface of the piezoelectric material layer includes a first plurality of spatially separated metal traces disposed thereon. The first plurality of metal traces are configured to include a transmission line and an active pad region. The second major surface of the piezoelectric material includes a second plurality of spatially separated metal traces disposed thereon. The second plurality of metal traces are configured to include a transmission line and an active pad region. Each of the second plurality of traces are positioned such that it is aligned with a corresponding one of the first plurality of separated metal traces to define a corresponding pair of opposing metal traces with an individually operable electrical excitation path therebetween. The package also includes a plurality of depressed wells formed in the platform body. The wells are configured to hold a predetermined quantity of dry powder pharmaceutical drug therein. Each of the depressed wells is positioned on the platform body to substantially overlie a respective active pad region of one pair of corresponding first and second metal traces.

In a preferred embodiment, in operation, in response to application of an excitation voltage differential to a selected one of the individually operable electrical paths, the piezoelectric material layer at the active pad region deforms to thereby actively disperse the dry powder pharmaceutical drug from the depressed well. The package can include one or more of a sealed releasable polymer cap positioned to overlie the plurality of depressed wells and a non-reactive barrier positioned in each of the depressed wells to define a dry powder drug contact surface therein.

In a preferred embodiment, the multi-dose dry powder blister package is configured to be received in a dry powder inhaler. The dry powder inhaler comprises a housing and a control system positioned therein, wherein during operation, the housing is configured to be in fluid communication with a user and define a flow exit path therefrom. The control system comprises a controller configured to engage with a selected one of the individually operable electrical paths. The control system also includes a battery having a first voltage output operably associated with the controller and a transformer for increasing the first voltage to a desired excitation voltage operably associated with the controller and the selected individually operable electrical path. The control system also includes an airflow sensor positioned in the flow exit path, and is preferably positioned upstream of the depressed well in the flow exit path (the well is intermediate the sensor and the use). This positioning can reduce the deposition of drug particles on the sensor. In operation, the controller is configured to adjust the excitation voltage corresponding to predetermined parameters associated with the dispersion of the dry powder drug.

In a preferred embodiment, the controller is programmed with a fuzzy logic system representing at least one of flow characteristics of the dry powder drug and the inspiratory capability of the user such that the excitation voltage transmitted to the selected electrical path is responsive to the results of the fuzzy logic system.

Similar to the first aspect of the invention described above, another aspect of the invention is directed to a disposable multi-dose dry powder package, with at least one integrated active element formed thereon. The dry powder package comprises a piezoelectric polymer firm having a substantially planar profile and an upper and lower surface. A first metal trace pattern is positioned onto the upper surface. The first metal trace pattern has a plurality of first pad regions and a plurality of first linear transmission lines. Each first pad region is connected to a respective one of the first linear transmission lines. A second metal trace pattern is positioned onto the lower surface. The second metal trace pattern has a plurality of second pad regions and a plurality of second linear transmission lines. Each second pad region is connected to a respective one second linear transmission line. The first and second metal trace patterns are aligned across the piezoelectric polymer material layer. The package also includes a plurality of individual quantities of dry powder drug positioned to substantially overlie each of the first pad regions on said upper surface. A sealant layer is positioned to overlay each of the unitized quantities of the dry powder drug to secure it in the disposable dry powder package.

In one embodiment, the piezoelectric polymer film is a thin film PVDF, and a backing material layer can be positioned to overlie a substantial portion of the lower surface of the PVDF.

Another aspect of the present invention is a method of dispersing an inhalable quantity of a dry powder pharmaceutical drug into a patient's airstream. The method includes the steps of positioning and holding a dry powder inhaler such that tit is in fluid communication with a user and ready to direct a quantity of dry powder pharmaceutical drug into the air stream of a user during inhalation, wherein the package holds at least one unitized quantity of dry powder pharmaceutical drug in a receptacle portion of thereon, the receptacle portion including a piezoelectric polymer material layer. The method also includes the steps of repeatedly applying a voltage differential across the piezoelectric polymer film in the region of the receptacle to deform the receptacle and expelling the dry powder drug held in the receptacle portion of the package such that it is dispersed into the air stream of a user during the user's inspiratory inhalation cycle.

Preferably, the deforming step is carried out by flexing the piezoelectric material in the region of the receptacle portion. The applying step can be carried out by providing a voltage of about 100–200 volts peak to peak across the piezoelectric layer. The voltage can be applied at various frequencies such as at a relatively low frequency of between about 3–60 Hz and/or a higher frequency of between about 25 kHZ to about 2 MHz.

The method can also include the step of measuring the inspiratory air flow rate of a user and controlling the voltage applied during said applying step responsive to the user's inspiratory flow rate obtained from said measuring step. The method can also include the step of forming the exit flow channel to provide or increase the turbulence of the airflow, particularly proximate the well.

The user's air flow rate can be established proximate to active dispensing of the dry powder drug (near the start of the inhalation cycle), it can be established based on an average air flow rate measured during prior uses, or on air flow rates obtained dynamically through the inhalation cycle.

The method can also include the step of defining a fuzzy logic function representing at least one predetermined condition. The at least one condition is associated with at least one of the configurations of the dry powder inhaler, the inspiratory ability of a user, flowability of the formulation of the dry powder pharmaceutical drug being administered, and respirable particle fraction data associated with the dry powder formulation. The method can also include the steps of determining the degree of membership for the at least one condition to the defined fuzzy logic function and adjusting the excitation voltage applied during the applying step based on the defining and determining steps.

Preferably, the fuzzy logic function controls the voltage output delivered during the applying step. The method can also include the steps of programming the dry powder inhaler with a computer readable program code which identifies a range of operational excitation output pulses having associated frequencies, amplitudes, and signal patterns associated therewith, and programming the dry powder inhaler with computer readable code which defines operational excitation output pulses suitable for predetermined types of dry powder drug formulations. The predefined ranges can speed up the selection or analysis process of the controller by limiting the range of operation of the device by narrowing the excitation pulses selectable based on the identified dry powder drug being dispensed and/or for particular types of systemic delivery targets.

An additional aspect of the present invention, similar to the method described above, is directed to a method of facilitating the dispersion of a dose of a dry powder drug into an inhalation delivery path. The method includes the steps of positioning a quantity of dry powder drug in a package having a piezoelectric polymer material layer, the piezoelectric polymer material layer having a plurality of receptacle regions configured and sized to hold the dry powder drug (in unitized quantities) proximate thereto, the piezoelectric polymer material layer configured with a plurality of selectively excitable regions corresponding to the plurality of receptacle regions. The method also includes the step of selectively applying an excitation signal to at least one of the selectively excitable regions to rapidly flex the piezoelectric polymer material layer threat to deform at least one receptacle region to thereby facilitate the dispersal of the dry powder drug into the inhalation delivery path.

Yet another aspect of the present invention is directed to a method of controlling a dry powder inhaler. The method comprises the steps of providing a dry powder inhaler having an active delivery system and an air flow sensor positioned in the exit flow path, measuring the air flow rate associated with the inspiratory efforts of a user using dry powder inhaler proximate to the desired administration of the dry powder drug, and adjusting the energy directed to the active delivery system responsive to the measuring step to thereby facilitate increased dose dispersion uniformly corresponding to the capabilities of a use.

An additional aspect of the present invention is a method of controlling the active delivery of a dry powder drug in an inhaler configured with an active energy assisted drug dispersion system. The method comprises the steps of establishing a priori a flowability characterization of a plurality of dry powder drug formulations. The airflow rate of a user using the dry powder inhaler is measured. A degree of membership of the flowability of the drug to be dispersed is determined utilizing a first fuzzy logic function. A degree of membership of the measured airflow rate of the user with a second fuzzy logic function is determined. The excitation signal directed to the active energy system of the inhaler is controlled based on the determined degrees of membership.

Another aspect of the present invention is directed to a method of fabricating a disposable multi-dose dry powder package which has at least one (and preferably a plurality of individually activatable elements) integrated active element formed thereon. The method comprises the steps of forming a package with at least one piezoelectric polymer film layer into a desired geometric shape with an upper and lower surface, dispensing a quantity of dry powder drug to substantially overlie a plurality of spatially separate selected upper surface regions of the piezoelectric polymer film layer, and sealing the dispensed dry powder drug to secure it against the dry powder package.

The method can also include the steps of forming a first metal trace pattern on the upper surface, the first metal trace pattern having a plurality of pad regions, and a plurality of linear transmission lines, a respective one connected to each of said pad regions; and forming a second metal trace pattern onto the lower surface, the second metal trace pattern having a plurality of pad regions, and a plurality of linear transmission lines, a respective one connected to each of said pad regions.

In addition, the method can include forming two piezoelectric polymer film layers, the layers separated by an intermediately positioned pliable core, all of which are concurrently deformable by the application of voltage thereacross.

The present invention can also employ a baffle or irregular shaped walls in the entrainment tube (exit flow channel) of the inhaler to facilitate turbulent air flow to increase the fraction of the powder emitted or dispersed from the device to the user.

Yet an additional aspect of the present invention is a computer program product for directing the operation of a dry powder inhaler to actively facilitate the dispersion of a dry powder drug into the exit flow path of the inhaler and into the inhalation flow path of the user. The computer program product comprises a computer readable storage medium having computer readable program code embodied in the medium, the computer-readable program code comprising computer readable program code which controls an excitation pulse transmitted to an active delivery mechanism in a dry powder drug inhaler configured with an active energy assisted drug dispersion system. The computer readable program code also comprises computer readable program code which defines a fuzzy logic analysis model to control the amount of energy delivered to the active energy system and computer readable code which determines the degree of membership of a dry powder drug to be administered to a first fuzzy logic function associated with the flowability of the dry powder drug. The computer readable program code also includes computer readable code which adjusts at least one of the type, frequency, or size of the excitation signal directed to the active energy system of the inhaler based, at least partially, on the determined degree of membership to the first fuzzy logic function.

In a preferred embodiment, the computer program product also includes computer readable program code which measures the airflow rate of a user's inspiratory efforts proximate to active dispersion of the dry powder drug into the exit flow path of the inhaler, and also includes computer readable program code which defines the fuzzy logic analysis model to adjust the excitation signal delivered to the active energy system includes computer readable code means for analyzing the user's measured airflow rate.

The computer program product can also include computer readable program code which considers one or more of the type of excipient used in the dry powder formulation, the cohesiveness of the dry powder drug, the geometry of the inhaler, and the systemic delivery target in determining the excitation pulse to be transmitted.

Advantageously, the present invention may provide more reliable and uniform inspiratory delivery of dry powder drug treatments with improved operational characteristics. The DPI, the PVDF blister package, and the fuzzy logic control system of the instant invention can provide one or more of the following advantages over conventional DPIs: reproducible dosing, emission of a high percentage of particles in a respirable size range, reduced opportunity for accidental multiple dosing, ease of operation, protection of the drug powder mixture from humidity, and reduced cleansing requirements.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, components, layers, or regions may be exaggerated for clarity.

Generally described, the present invention is directed to dry powder inhalers with integrated, active energy, patient-assisted dispersal systems which are configured with control systems that provide adjustable energy output to the active dispersal element responsive to a user's inspiratory capabilities and/or the flowability of the dry powder drug being administered. The inhalers can be used for nasal and/or oral (mouth) respiratory delivery. Preferably, the inhalable dry powder dose is packaged in a multi-dose dry powder drug package which includes a piezoelectric polymer substrate (such as PVDF) that flexes to deform rapidly and provide mechanical oscillation in an individually selectable signal path on the package. The signal path directs the signal to the region of the drug receptacle or well to cause the well to oscillate in cooperation with a user's inspiratory effort, and, thus, actively direct the dry powder out of the well and up into the exit flow path. As a result, the powder is actively dispersed into the exit flow path of the inhaler during the user's inspiratory activity. The dry powder inhaler can also employ control systems with fuzzy logic models of the flowability of particular drug formulations (which may also be able to compensate or allow for the particular type of excipient or other additive used) and systems which can adjust for the real-time measured inspiratory effort's of the user.

Figure 1:
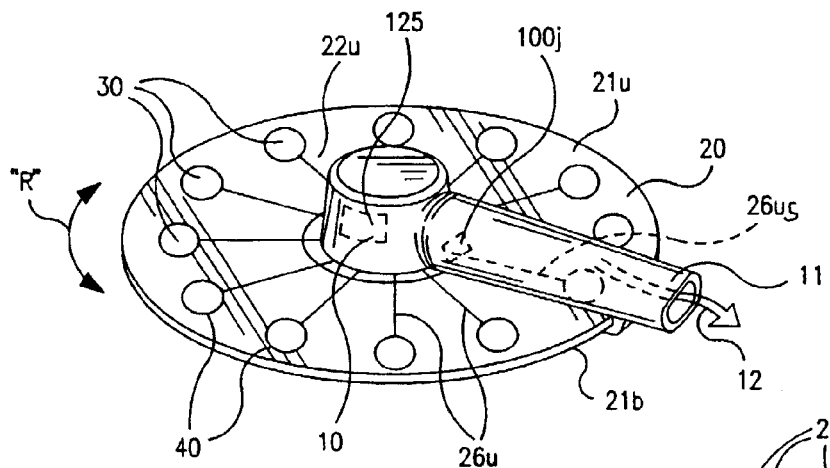
FIG. 1 is a perspective view of a DPI according to the present invention.
Figure 2:
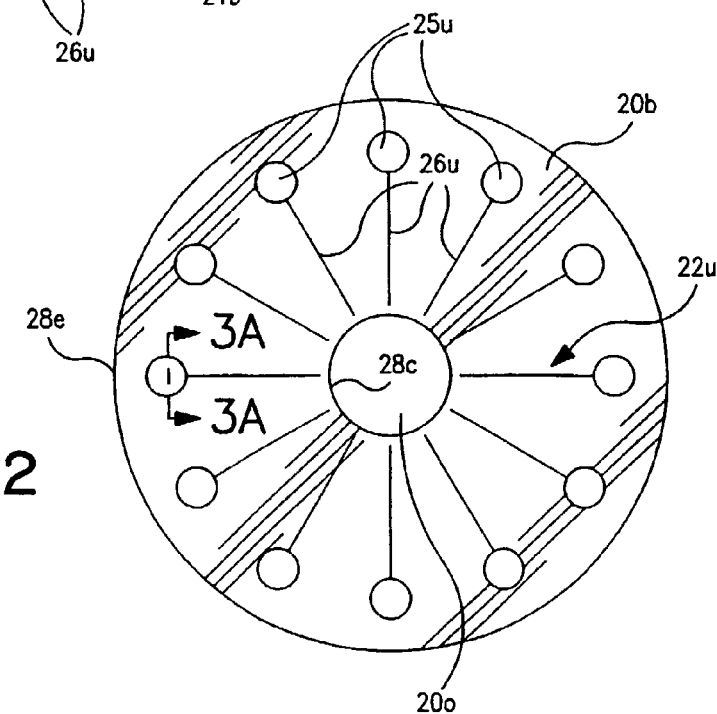
FIG. 2 is a top view of a dry powder blister package that is insertable into the DPI of FIG. 1 according to the present invention.
Figure 3A:
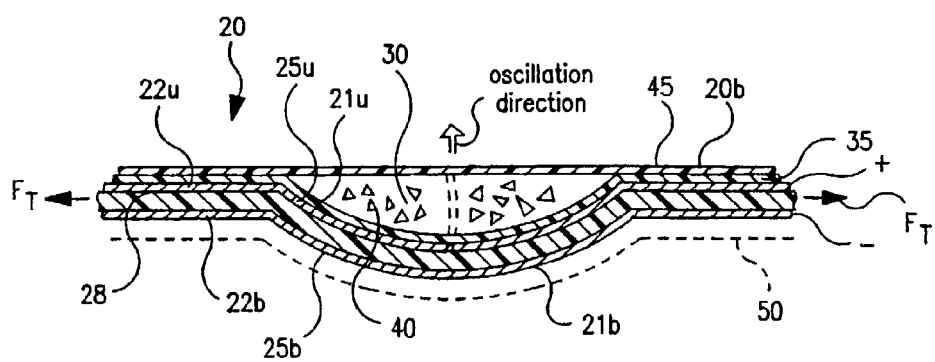
FIG. 3A is a partial section view taken across line 3A—3A in FIG. 2.

Referring now to FIG. 1, one embodiment of a DPI 10 configured to receive and orally dispense the inhalable dry powder from a multi-dose dry powder drug package 20 is illustrated. Examples of suitable dry powder drug packages 20 are also shown in FIGS. 2 and 3A. As shown, the multi-dose dry powder drug package 20 includes a platform body 20b with integrated active elements formed by corresponding upper and lower metal trace patterns 22u, 22b, which are disposed on a piezoelectric substrate material layer 28. The platform body 20b includes a first metal trace pattern 22u on the upper surface 21u of the platform body 20b. As shown, the first metal trace pattern 22u includes a plurality of spaced-apart pads 25u and a corresponding transmission line 26u connected to and extending away from each of the active pads 25u. The bottom of the platform body 21b includes a second metal trace pattern 22b (FIG. 3A). Preferably, the second metal trace pattern 22b is substantially the same as the first 22u and symmetrically arranged such that the patterns are aligned the first over the second with the piezoelectric substrate layer 28 in between.

Referring now to FIGS. 1 and 2, a plurality of unitized or individual doses of a dry powder formulation mixture 30 are arranged on the platform body 20b such that each dose resides against and substantially overlies a respective active contact pad 25u. For clarity, it will be understood that, according to the present invention, protective films, moisture protective barriers, drug protective barriers or coatings may also be positioned over the substrate layer 28, the traces 22u, 22b, or other portions of the platform body 20b. Preferably, if applied proximate the active oscillation region/wells 40, they are applied so as to be substantially transparent to the operation of the active elements. Preferably, as shown in FIG. 3A, an inert or nonreactive barrier 35 is disposed over at least the upper pads 25u to protect the purity and stability of the dry powder drug from potential contamination of or interaction with the dry powder drug which contacts and resides on this surface. In a preferred embodiment, the inert or non-reactive barrier 35 is a thin polymer cover or coating material which is applied onto the upper surface of the platform body 20b such that, in operation, it is substantially concurrently responsive to the deformation of the piezoelectric substrate layer 28.

Figure 3B:
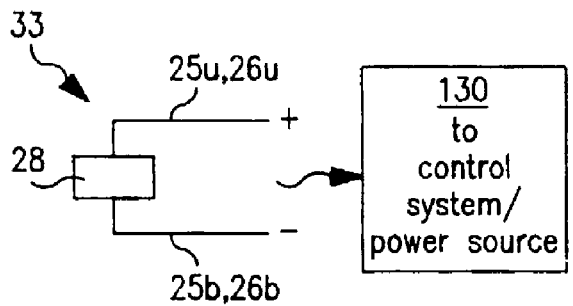
FIG. 3B is a schematic diagram of an individually selectable electrical excitation path configured on a dry powder blister package with a single piezoelectric substrate layer according to the present invention.

Referring again to FIG. 3A, it is also preferred that the first and second metal trace patterns 22u, 22b are each in contact with, and aligned across, the piezoelectric substrate layer 28. That is, the first metal trace pattern 22u is oriented on a first major surface of the piezoelectric substrate layer 28 such that it substantially overlies the second metal trace pattern 22b to define pairs of corresponding transmission lines 26u, 26b and active pads 25u, 25b. As schematically represented in FIG. 3B, in operation, each pair of corresponding transmission lines 26u, 26b and active pads 25u, 25b can provide an individually excitable electrical excitation path 33.

As is also shown in FIG. 3A, it is preferred that the platform body 20b is configured so as to provide a plurality of drug holding receptacles or depressed wells 40. As shown, the wells 40 are configured to hold a dose or single-sized bolus quantity of a dry powder drug 30. In a preferred embodiment, the wells 40 are defined by concave contours formed in the piezoelectric substrate layer 28. It is also preferred that the dry powder drug 30 be sealed in the well by a sealant layer 45 such as a polymer cap. When the multi-layer package is secured together after filling with the desired drug, the package is configured such the at the attached platform body layers, including the opposing active pads 25u, 25b, and the nonreactive barrier 35, (and optionally the backing layer 50) have a conformal concave shape. That is, each layer substantially follows the shape of the piezoelectric substrate layer material 28. Stated differently, in operation, each of the layers 35, 25u, 28, 25b move in concert during application of the excitation signal across the piezoelectric substrate layer 28. Other non-circular receptacle configurations can also be employed such as, but not limited to, oblate or prolate spheroids.

As is also shown in FIG. 3A, an optional backing layer 50 can also be applied to the underside of the platform body 20b. Again, it is preferred that the backing layer 50 be applied such that it is conformal to the piezoelectric substrate layer 28 and moves in concert therewith during activation of the selected well 40. This backing layer 50 can help amplify the oscillation of the receptacle or well 40 caused by the application of the excitation signal across the piezoelectric substrate layer 28 by providing amplifying weight opposite the powder surface. Examples of materials suitable for the backing layer 50 include, but are not limited to, polyvinylchloride ("PVC").

Figure 11A:
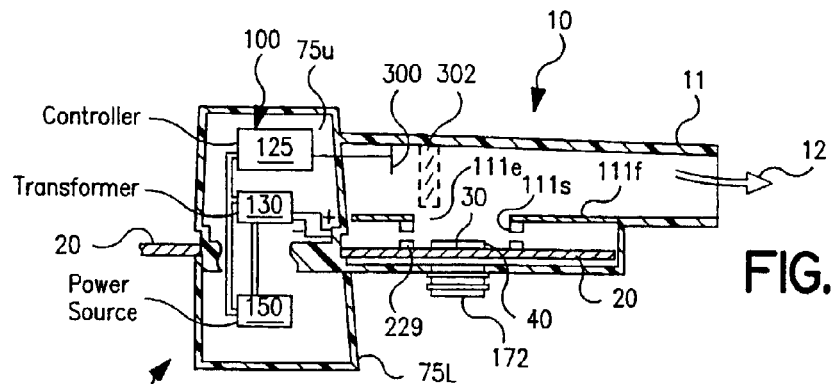
FIG. 11A is a side cutaway view of a DPI illustrating an integrated control system according to the present invention.
Figure 11B:
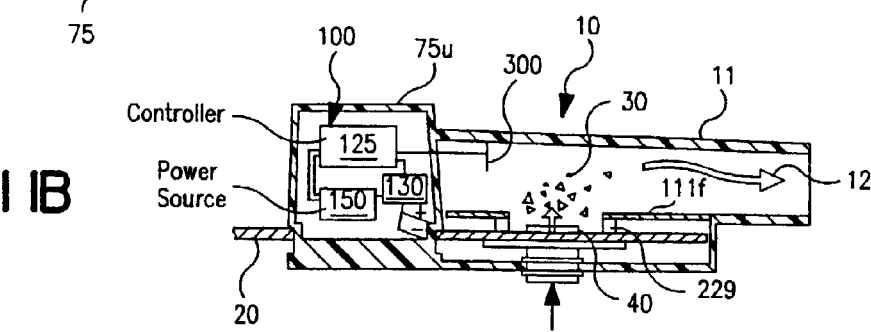
FIG. 11B is a side cutaway view of the DPI shown in FIG. 11A with the blister package raised to be positioned in the inhaler airstream exit passage so that the dry powder drug is actively dispersed into the inspiratory air path and directed out of the inhaler.
Figure 11C:
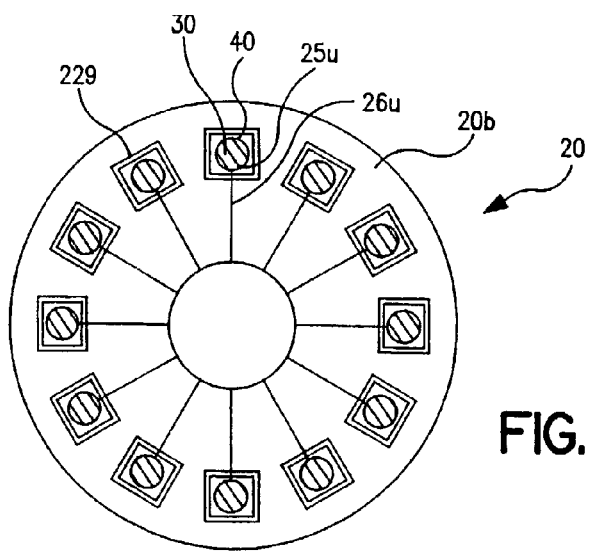
FIG. 11C is a top view of an alternate embodiment of a circular platform blister package according to the present invention showing seals positioned around the perimeter of the drug wells.

As shown in FIG. 1, the transmission lines 26u extend radially inward toward the center of the package 20 where the portion of the DPI 10 holding the controller 125 and the power source 150 (see FIG. 11A) is located (preferably at least a 5 Vp-p or 9V button type batter). Similarly, the bottom transmission lines 26b also extend toward the center of the package 20. In this embodiment, the center of the package includes an aperture or opening 20o formed therein (FIG. 2). As shown in FIG. 11A, the DPI 10 is configured with top and bottom portions 75u, 75l and the center opening 20o of the package 20 allows easy electrical connection between components held in the bottom portion of 75l with those held in the top portion 75u. FIGS. 11A and 11B also illustrate that the DPI housing 75 can be configured with or without a lower portion 75l.

When assembled to the DPI 10 illustrated in FIG. 1, the transmission line ends adjacent the center opening 20o in the inhaler chamber 11 are individually electrically activatable by the controller 125 in the DPI 10 and, thus, define the selected corresponding transmission line pair 26$u_s$, 26$b_s$, and the associated electrical excitation signal path or circuit 33. The transmission lines 26$u_s$, 26$b_s$, connect in the DPI housing 75 at an electrical junction (schematically illustrated by box 100$j$) which provides the signal/ground or +/− connections to the appropriate side (the upper or lower transmission lines 26$u$, 26$b$) of the drug package 10. The junction can be formed in a number of ways such as by traces disposed onto surfaces, flex circuits, wiring, and the like.

The control system 100, thus, preferably acts to electrically activate selected transmission lines 26$us$, 26$bs$ and the control system 100 can send the excitation signal to selectively cause the mechanical oscillation at the associated well 40 region of the package 10. Because only the selected transmission lines are electrically connected to the energy source, the other non-selected drug wells 40 remain static (not electrically activated and electrically isolated from mechanical oscillation). As the next dose in the sealed well 40 is rotated into the inhalation chamber 11 (which defines the exit flow path 12 from the DPI 10), a puncturing means (not shown) positioned proximate the inhalation chamber 11 can remove the sealant to expose the dry powder drug 30 in the well 40 to allow the drug to be freely dispersed when the well 40 is oscillated as described above. The rotation is illustrated in FIG. 1 by the letter "R". The direction of rotation can be either clockwise or counter clockwise.

As noted above, the dry powder formulation mixture can be a single ingredient or a plurality of ingredients, whether active or inactive. The inactive ingredients can include additives added to enhance flowability or to facilitate delivery to the desired systemic target (such as additives to inhibit premature deposit in the respiratory system (such as the mouth) during inhalation). The dry powder drug formulations can include active particulate sizes which vary. The device may be particularly suitable for dry powder formulations having particulates which are in the range of about 0.5–50 $\mu$m, and preferably in the range from about 0.5 $\mu$m–20.0 $\mu$m, and more preferably in the range of about 0.5 $\mu$m–8.0 $\mu$m. The dry powder formulation can also include flow-enhancing ingredients, which typically include particulate sizes, which are larger than the active ingredient particulate sizes. Preferably, the flow-enhancing ingredients comprise excipients having particulate sizes on the order of about 50–100 $\mu$m. Preferred excipients include lactose and trehalose. Other types can also be employed such as sugars which are approved by the United States Food and Drug Administration ("FDA") as cryoprotectants (e.g., mannitol) or as solubility enhancers (e.g., cyclodextrine) or other generally recognized as safe ("GRAS") excipients.

The dry powder treatments can be used to treat asthma, influenza, and other respiratory ailments. As noted above, there is also an interest in expanding this administration concept to include the delivery of antimicrobial agents such as antitubercular compounds, proteins such as insulin for diabetes therapy or other insulin-resistance related disorders, nucleic acids or ogligonucleotides for cystic fibrosis gene therapy and peptides such as leuprolide acetate for treatment of prostate cancer and/or endometriosis. Typical dose amounts of the unitized dry powder mixture dispersed in the inhaler will vary depending on the patient size, the systemic target, and the particular drug. An exemplary dry powder dose amount for an average adult is about 20 mg and for an average adolescent pediatric subject is from about 5–10 mg.

Exemplary dry powder drugs include, but are not limited to, albuterol, fluficasone, beclamethasone, cromolyn, terbutaline, fenoterol, β-agonists, and glucocorticoids.

Advantageously, as the active elements are integral to/included as part of the disposable drug package 20, unlike many conventional active dispersion systems, cleansing of the active mechanism portion of the inhaler is no longer required.

Referring again to FIG. 3A, the piezoelectric substrate layer 28 is a piezoelectric polymer material. In a preferred embodiment, the piezoelectric polymer film is formed from a piezoelectrically active material such as PVDF (known as KYNAR piezo film or polyvinylidene fluoride) and its copolymers or polyvinylidene difluoride and its copolymers (such as the PVDF with its copolymer trifluoroethylene (PVDF-TrFe)).

In a preferred embodiment, the piezoelectric substrate layer 28 is a thin film PVDF. As used herein, the term "thin film" means that the piezoelectric substrate layer 28 is configured as a structurally flexible or pliable layer which is preferably sized to be about 10–200 $\mu$m thick.

The metal trace patterns 22$u$, 22$b$ are preferably provided by applying a conductive pattern onto the outer faces of the piezoelectric substrate layer 28. For depositing or forming the metal trace patterns 22$u$, 22$b$, any metal depositing or layering techniques can be employed such as electron beam evaporation, thermal evaporation, painting, spraying, dipping, or sputtering a conductive material or metallic paint and the like or material over the selected surfaces of the piezoelectric substrate (preferably a PVDF layer as noted above). Of course, alternative metallic circuits, foils, surfaces, or techniques can also be employed, such as attaching a conductive mylar layer or flex circuit over the desired portion of the outer surface of the piezoelectric substrate layer 28. It is preferred that, if flex circuits are used, that they are configured or attached to the substrate layer 28 so as to be substantially transparent to the structure of the sensor array to minimize any potential dampening interference with the substrate layer 28. It is also noted that while particular conductive patterns are illustrated in the figures, the present invention is not limited thereto, as alternative conductive patterns may also be used.

Figure 12:
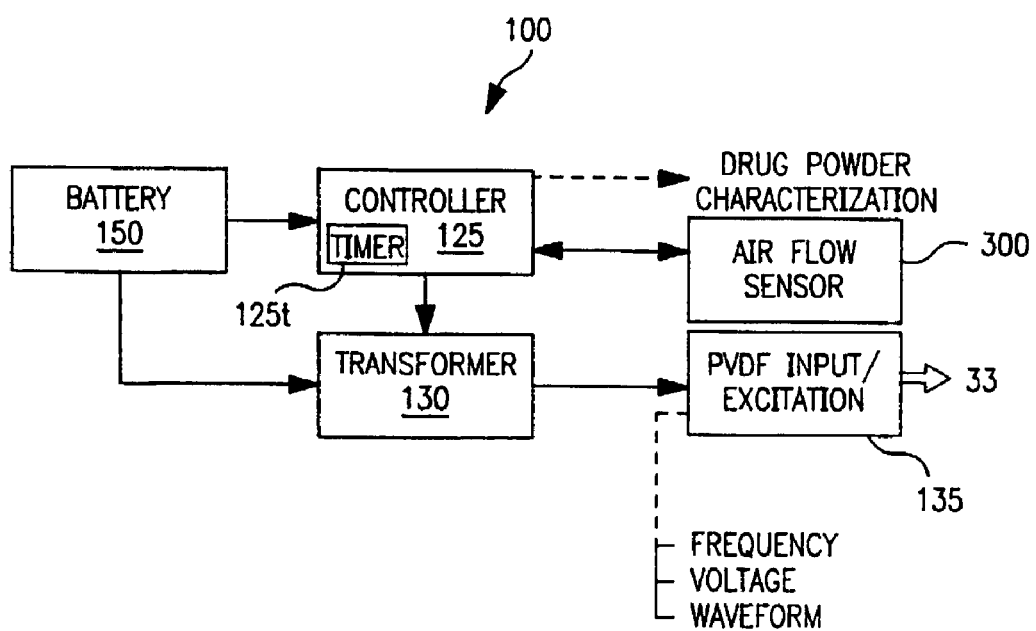
FIG. 12 is a block diagram of a control system for a DPI according to the present invention.

Preferably, the upper and lower surface metal trace patterns 22$u$, 22$b$ do not connect on the platform body 20$b$. For example, the conductive paint or ink (such as silver or gold) is applied onto the major surfaces of the platform body 20$b$ such that it does not extend over the perimeter edge portions 28$e$ of the piezoelectric substrate layer 28, thereby keeping the metal trace patterns on the top and bottom surfaces 22$u$, 22$b$ separated with the piezoelectric substrate layer 28 therebetween. This configuration forms the electrical excitation path when connected to a control system 100 (FIG. 12) to provide the input/excitation signal for creating the electrical field that activates the deformation of the piezoelectric substrate layer 28 during operation. As such, the electrical path 33 for each pad 25$u$, 25$b$ extends via the respective transmission line 26$u$, 26$b$ to the electrical terminations operably connected to the controller 125 (FIG. 12).

Referring again to FIGS. 3A and 3B, the excitation circuit configuration 33 can be such that the upper trace operates with a positive polarity while the lower trace has a negative polarity or ground, or vice versa (thereby providing the electric field/voltage differential to excite the piezoelectric substrate in the region of the selected well 40). Of course, the polarities can also be rapidly reversed during application of the excitation signal (such as + to −, + to −) depending on the type of excitation signal used.

Figure 4:
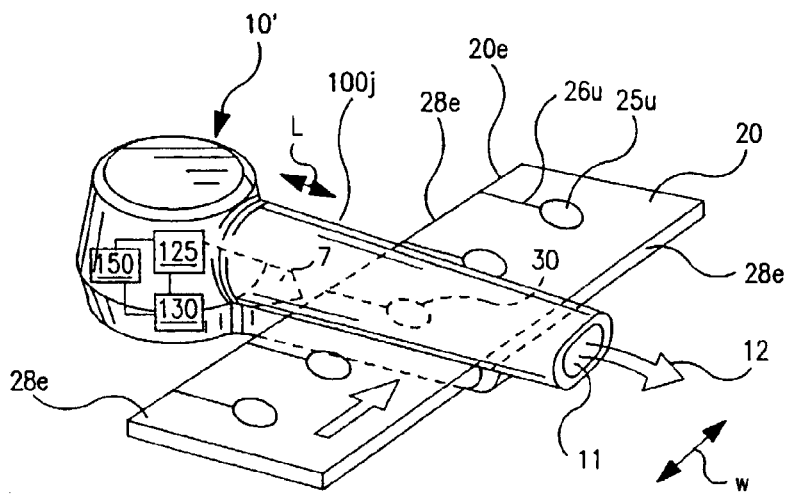
FIG. 4 is a perspective view of an alternate embodiment of a DPI according to the present invention.

FIG. 4 illustrates an alternative embodiment of a DPI designated broadly at 10'. As shown, the housing of the DPI 10' is configured to receive a linearly configured dry powder package 20 therein. Similarly, the transmission lines 26*u* thereon extend laterally toward an edge of the platform body 20*e* to allow electrical connection with the power source 150 and the controller 125 in the DPI 10'. In this embodiment, instead of rotating the package 20 such that the next dose of the dry powder drug 30 is moved into the inhalation chamber 11, the drug package 20 can be translated in a direction which is perpendicular to the direction of the transmission lines 26*u* into position. As above, a serrated edge or other tearing or puncturing means can be positioned on or proximate the inhalation chamber to expose the well to allow the dry powder drug to be freely dispersed. Of course, the sealant layer 45 may also be manually removed.

Figure 5A:
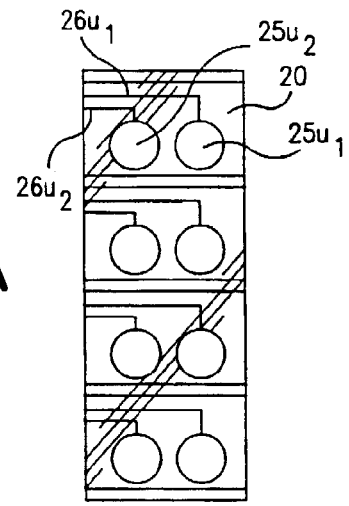
FIGS. 5A–5C are top views of alternate embodiments of linear platform multi-dose blister packages according to the present invention.
Figure 5B:
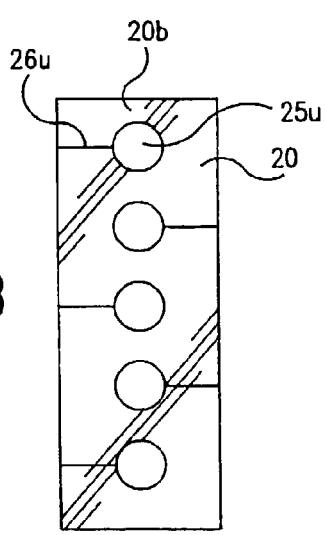
Figure 5C:
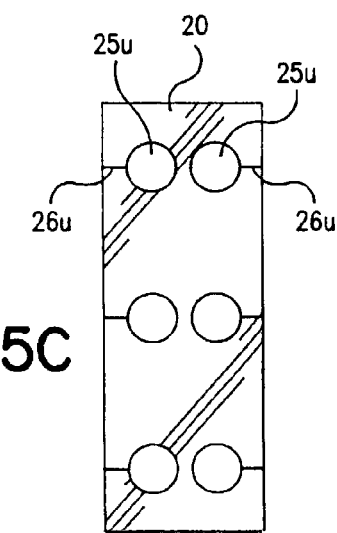

FIGS. 5A, 5B, and 5C illustrate exemplary alternate embodiments of a multi-dose dry powder drug package with active elements. FIG. 5A illustrates that instead of a single well ro single excitation pad used to dispense a single use dose as describe above, the package 20 can be configured with two separate pads 25*u*1, 25*u*2. As above, the bottom metal trace patterns are substantially similarly configured and, preferably a symmetrical image of the first trace pattern. These two separate pads 25*u*1, 25*u*2, (with their respective bottom pads 25*b*1, 25*b*2) as shown are aligned along the length direction (shown as the axis marked as "L") of the inhalation chamber 11. They can also be alternatively configured, such as, being aligned along the width direction (shown by the axis marked as "W" in FIG. 4), and/or offset a distance about the "L" axis but configured to be positioned within the inhalation chamber 11 to be dispersed together during a single inspiratory dispensing activity by the user. That is, each pad 25*u*1, 25*u*2 (and 25*b*1, 25*b*2) via their respective transmission lines 26*u*1, 26*u*2 (26*b*1, 26*b*2), is activated concurrently to disperse their doses into the exit flow path 12. Because smaller quantities are dispensed from two wells 40 in the inhalation chamber 11 (dispensing the same overall single held dose), less energy may be needed and/or a more uniform dispersion may be achieved (or even holding two ingredients that can be jointly administered that are separated before use).

Figure 6A:
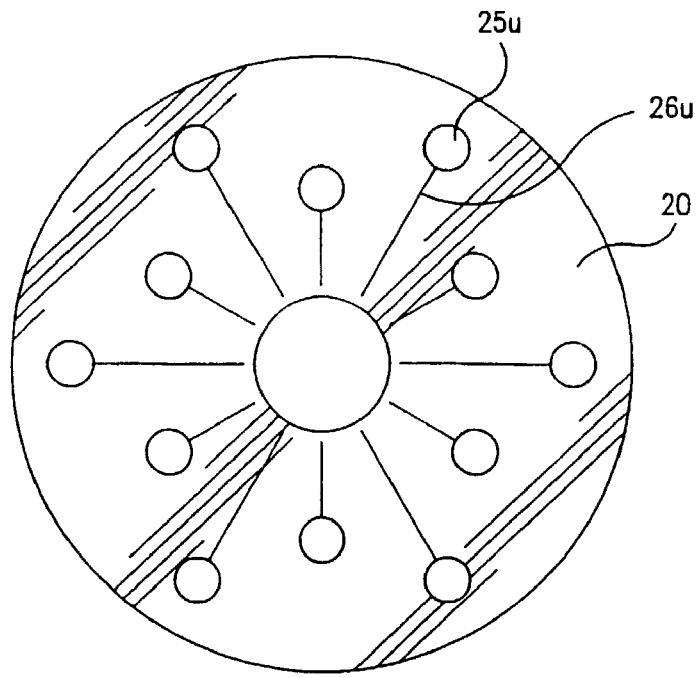
FIGS. 6A and 6B are top views of alternate embodiments of circular platform blister packages according to the present invention.
Figure 6B:
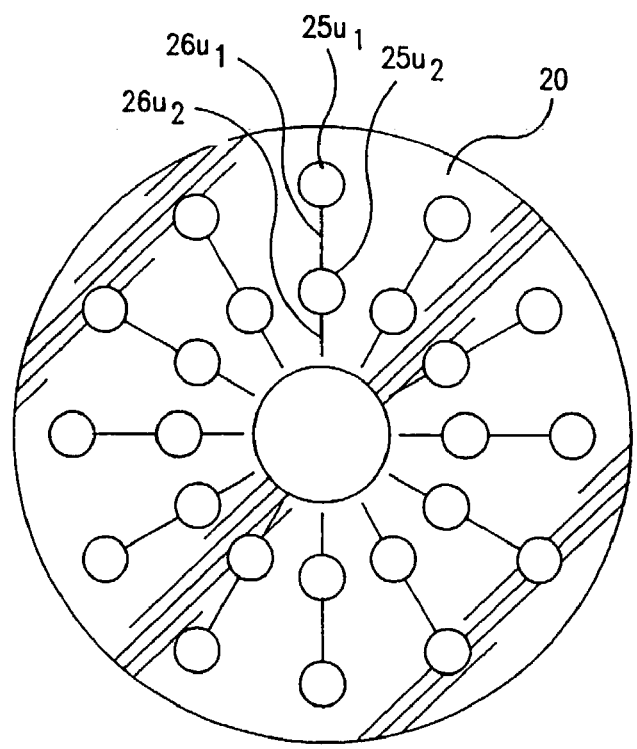
Figure 7A:
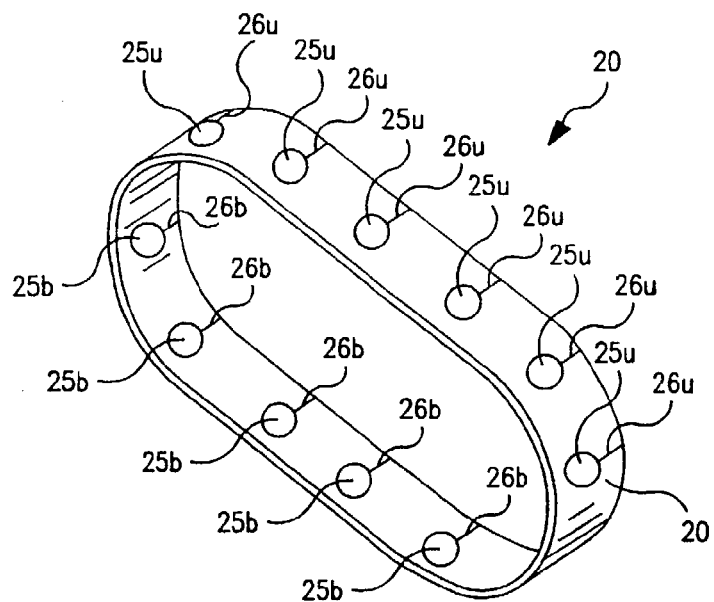
FIGS. 7A and 7B are side perspective views of endless linear platform blister packages according to additional embodiments of the present invention.
Figure 7B:
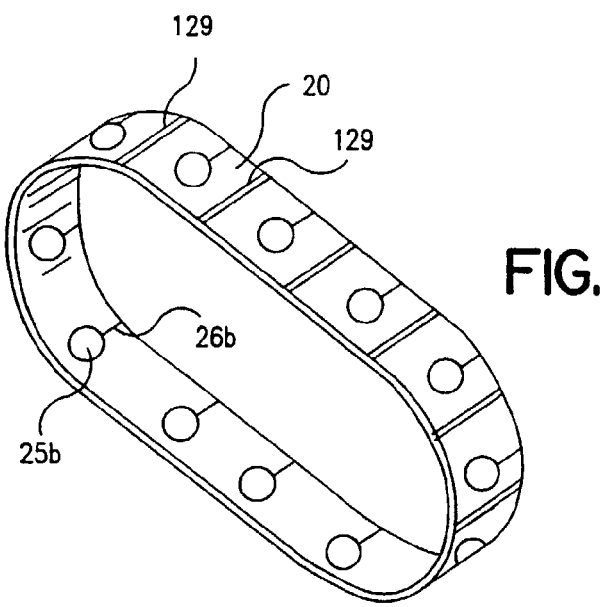
Figure 8A:
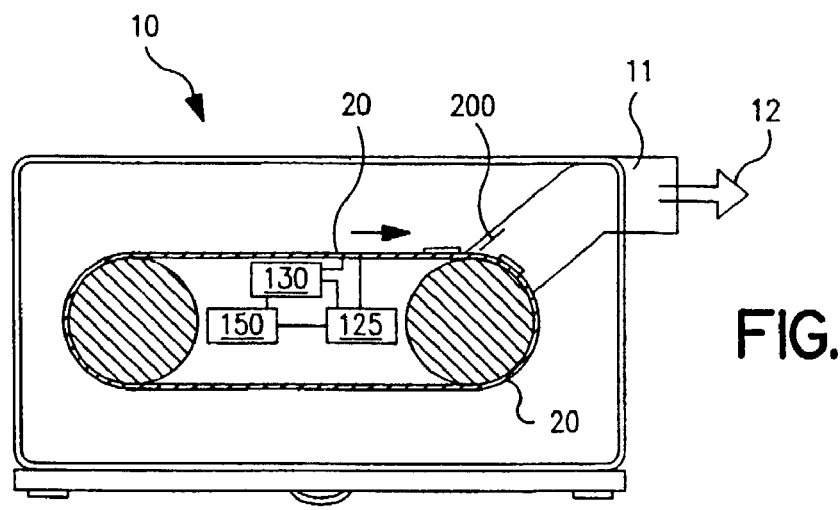
FIGS. 8A, 8B, and 8C are cutaway views of alternative DPI embodiments configured to receive endlessly configured blister packages such as those shown in FIGS. 7A and 7B therein.
Figure 8B:
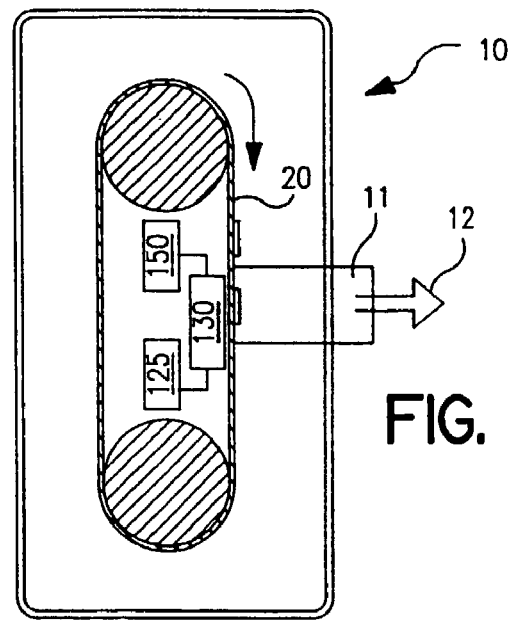
Figure 8C:
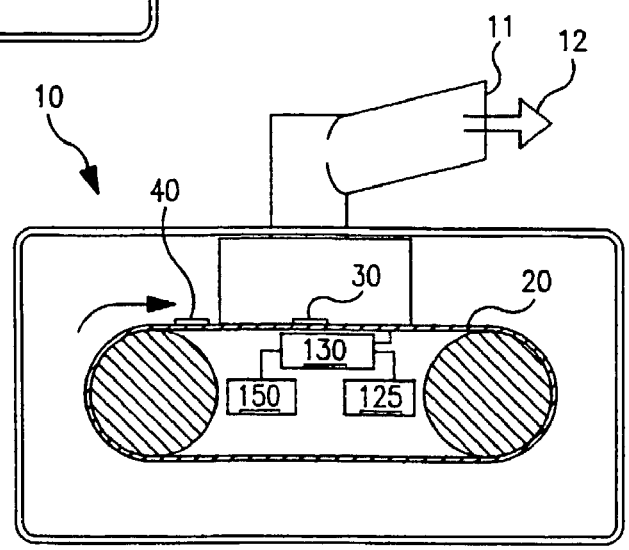

FIG. 5B illustrates that the transmission lines 26*u*, 26*b* can be alternately located against alternating edges of the platform body 20*b*. FIG. 5C illustrates that the pads and transmission lines 25*u*, 26*u* (and correspondingly 25*b*, 26*b*) can be arranged such that after doses are dispensed along one side of the package 20, it can be turned, reinserted, and activated along the other side (providing an increased density drug dispensing package). FIGS. 6A and 6B illustrate similar configurations for the circular package embodiment of the multi-dose package 20. Of course, although shown in FIGS. 5A and 6B with two concurrently excitable pads 25*u*1, 25*u*2 (25*b*1, 25*b*2) configured to be in the inhalation chamber, the package 20 can also employ greater numbers of pads in different combinations (such as one or more or combinations of pads that are side by side, serially aligned, offset, and the like). Similarly, instead of a plurality of separately excitable pads connected by transmission lines such as shown in FIGS. 5A and 6B, a single longer pad can be used with multiple wells formed therein (not shown).

FIGS. 7A and 7B illustrate yet another embodiment of a multi-dose dry powder drug package 20 with active elements according to the present invention. As shown the package 20 is an endless loop. FIG. 7B illustrates that the package 20 can also include sealing ridges 129 intermediate each well or upper surface pad 25*u*. The purpose of the sealing ridges 129 will be discussed further below.

FIGS. 8A–8C illustrate exemplary embodiments of a DPI (each designated at 10) configured to receive endless drug package 20 configurations (such as those shown at FIGS. 7A and 7B). As shown, the DPI 10 is configured to enclose the package 20 therein. As the package 20 rotatably advances (such as via known advancement means) a puncture means 200 proximate the inhalation chamber 11 and exit flow path 12 punctures the selected well 40. As shown, each embodiment includes an inhalation chamber 11 which is in fluid communication with the activated corresponding trace pair 25*u*, 25*b*, 26*u*, 26*b*. These inhalation chambers 11 can be configured with walls which extend a distance within the enclosure to reside against the drug package 20, such as at the sealing ridges 129 described above, to seal, at least partially, the inhalation chamber 11 to require less patient inspiratory effort. Alternatively, the entire enclosure or housing can define the inhalation chamber 11 (not shown).

FIGS. 10A–10C illustrate embodiments of a DPI (each designated at 10) configured to enclose, and preferably, seal, the circular multi-dose dry powder drug package 20 shown in FIGS. 2, 6A, and 6B. As shown in FIGS. 10B and 10C, the DPI body may be formed into whimsical shapes which may help make pediatric patients more receptive to the use of the device. FIG. 10B illustrates a science fiction-type spaceship design while FIG. 10C illustrates a turtle shell housing design. Other configurations such as a lady bug shell, baseball mitt and the like may also be suitable. Of course, other circular or generally circular designs such as sea shells, wheels, hats, animals and the like can also be employed.

FIGS. 11A–11B illustrate a partially sealable DPI 10. In this embodiment, an opening 111 in the lower floor 111*f* of the inhalation chamber 11 is configured to receive the drug well 40 of the package 20 therein. A user operable extension member 172 can be used to raise the package 20 into a sealed position against the lower floor 111*f* of the inhalation chamber. A seal 229 can be positioned around the perimeter of the well 40 on the package as shown in FIG. 11C. Similarly, a corresponding seal 111*s* can be positioned proximate to the opening of the inhalation chamber 11. As shown in FIG. 11B, when the extension member 172 pushes a portion of the package 20 into operative positions, the control system 100 makes electrical contact with the signal traces 25*u*, 25*b*, 26*u*, 26*b* to activate the dispersion of the powder 30 into the partially sealed inhalation chamber 11, directing the dry powder formulation out into the exit flow path 12. It may be desirable to configure the extension member 172 with a center portion which is pliable so that it can substantially conform to the piezoelectric substrate layer 28 (acting as a backing layer assisting the oscillation) (not shown). Alternatively, the extension member 172 may be configured with a central opening corresponding to the active drug region of the package to allow the well to oscillate without significantly impeding the movement of the well 40 (also not shown).

As also shown in FIGS. 11A and 11B, in a preferred embodiment, the DPI 10 includes an airflow sensor 300 positioned in the inhalation chamber 11. The airflow sensor 300 is electrically connected to the controller 125 in the control system 100. The airflow sensor 300 is used to measure the inspiratory efforts of a user. One suitable type of airflow sensor 300 is a "hot wire" configuration which employs electrical current which heats the wire corresponding to the amount of detected airflow. Other flow sensors can also be used as will be known to those of skill in the art. For example, flow sensors using impellers or beams can be suitable for use in the inhaler devices. It is also preferred that the airflow sensor 300 be configured slightly upstream of the drug well 40 (the drug well is intermediate the exit flow path and the sensor 300) so as not to interfere with the dispersion of the drug into the exit flow path 12. This position will also reduce the likelihood that (and/or the quantity) dry particles may be deposited onto the sensor during use.

FIG. 11A also illustrates the use of a baffle 302 positioned in the air flow path 12 proximate to (preferably just upstream) to extend across a portion of the airflow channel about the well 40. The baffle 302 disrupts the airflow pattern providing an airstream with turbulence which can enhance or cause a larger fraction of fine particle fraction of the powder particles to be emitted or dispersed from the device. The baffle 302 can be attached to the ceiling of the air flow channel and extend therefrom across a major portion of the airflow channel. In one embodiment, for an 17 mm wide airflow channel, the baffle can be a lightweight component (formed of sterilized Plexiglas or the like) configured and sized about 12 mm wide (2 mm in thickness) to fit within the flow channel while leaving about a 5 mm gap from the bottom (well region). Of course, other air flow channel turbulent flow configurations or components can also be used, such as forming the inner walls themselves with contours or shapes/features which promote/introduce turbulence in the airstream which can increase the quantity of fine particle fraction of particles ("FPF") emitted from the device.

Preferably, the airflow measurement is performed dynamically, during or just prior to the active dispersing of the dry powder drug 30. In addition, the airflow measurements taken by the DPI 10 can be stored in memory in the controller 125 and downloaded for analysis by a physician at a later date. This air flow measurement data can now provide real use data and can allow adjustment as to the type of inhaler best suited for a particular user, the type of drug dispensed, or even the configuration of the drug package (such as the prescription of an increased number of wells for concurrent dispersal of the drug dose as discussed above). This data can also allow for more customized treatment and/or delivery according to the particular inspiratory abilities of the user. In addition, this data may allow a physician to monitor the severity of or changes in the airflow impairment for asthmatic or respiratory ailments.

In any event, when at least one real time or dynamic measurement is taken, the data is fed back to the controller 125, which is programmed with logic which can adjust the excitation signal 135 delivered to the drug well 40 to increase or decrease the amount or degree of oscillation at the well. Alternatively, the controller 125 can receive the air flow measurement and adjust the next active energy excitation pulse based on a running average.

FIG. 12 illustrates a control system 100 according to one embodiment of the present invention. As shown, the control system includes a controller 125 (with a timer 125*t*), a battery power source 150, and a step-up transformer 130. The control system 100 also preferably includes the airflow sensor 300. In operation, the control system 100 controls the active dispersion of the drug by being able to adjust the excitation signal to the electrical signal path 33 based on selected parameters which correspond to the flowability of the drug. For example, the selected parameters can be one or more of the following: the type of drug being administered (the respective flowability of same along with the associated particulate size), the dose quantity in the well(s), the geometry of the inhaler, the presence or absence of additives in the drug formulation (such as excipients), the systemic delivery target, and the inpiratory capability of the user (preferably at the particular time of use). Many of these parameters may be defined a priori and programmed into the controller as a computer readable "look-up" table or operational program. Preferred control system logic systems will be discussed further below.

In operation, the piezoelectric substrate 28 acts as an electromechanical transducer and, as such, an oscillator. Generally described, and as shown in FIG. 3A, the well 40 is configured such that when the piezoelectric substrate layer 28 is subjected to an electric potential or voltage it deforms to flex proportionally to the magnitude of the electric field generated by the excitation signal across the thickness of the piezoelectric material. By rapidly exposing the selected well 40 to a changing voltage potential, the activated well 40 oscillates. The changing voltage potential may be provided by a number of excitation signals (some of which are continuous and have positive and negative polarities such as cosine, sine and other type waves, and some of which have one polarity, such as square waves).

Figure 9:
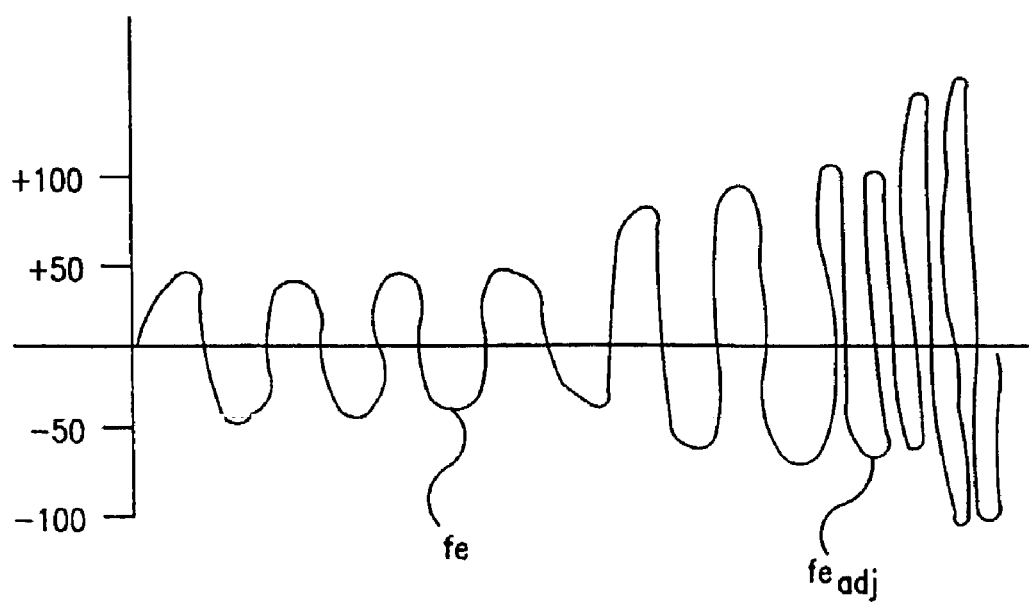
FIG. 9 is a graph illustrating an exemplary excitation signal having adjustable frequency and/or amplitude according to the present invention.
Figure 10A:
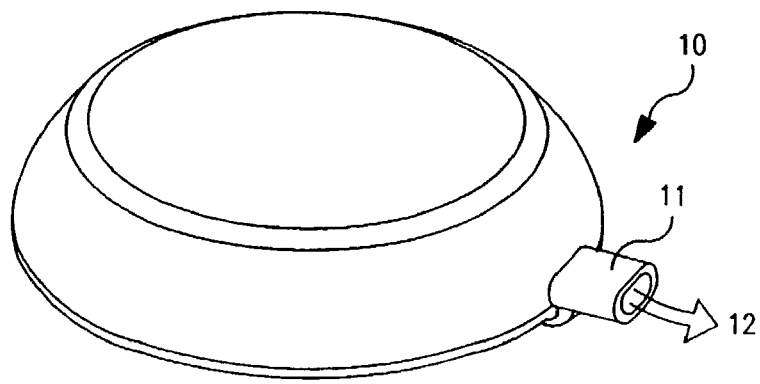
FIGS. 10A–10C are perspective views of alternate embodiments of DPI inhalers configured to enclose a blister package such as those shown in FIGS. 2, 6A, and 6B therein.
Figure 10B:
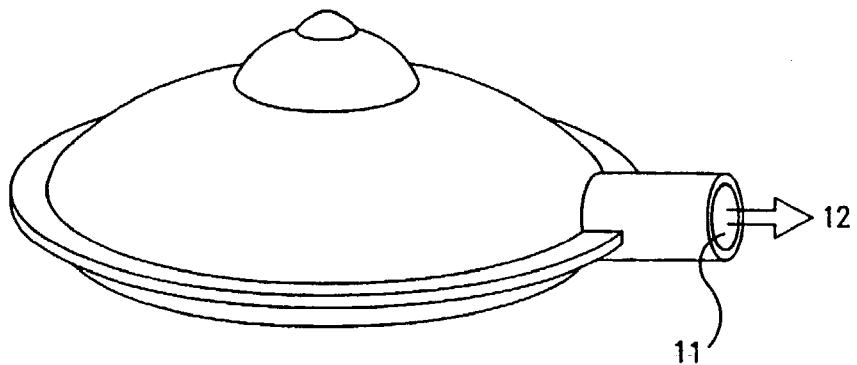
Figure 10C:
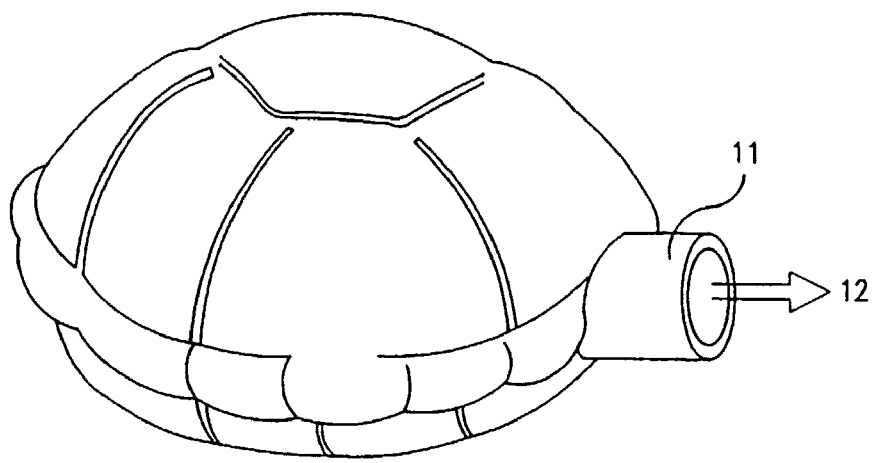

It is preferred that the input excitation voltage signal provide between about 50–300 volts peak to peak, and more preferably in the range of about 100–200 volts peak to peak voltage potential across the activated well 40 region (as shown in FIG. 9). The frequency of the excitation signal (an example of which is shown as $f_e$ in FIG. 9) and/or the amplitude of the excitation signal may vary, depending on certain factors such as the type of powder, the dose of the powder, the configuration of the dose package, and the presence of additives such as excipients and the like. Further, as is also shown in FIG. 9, the frequency and/or strength (amplitude) of the excitation signal can be adjusted $f_{eadj}$ during the inhalation cycle (the user typically having poorer inspiratory efforts during the latter portion of the inhalation cycle). Of course, the adjustment can be made based on real time airflow sensor measurements corresponding to the user's actual efforts.

In one embodiment, a low frequency excitation pulse can be used (i.e., a frequency between about 3–100 Hz, and more preferably between about 3–60 Hz). It is anticipated that this low frequency excitation signal will act to fluidize the dry powder into the exit flow stream. In another embodiment, particularly where flow additives are included in the drug formulation, it is preferred that higher frequencies be used (for example, about 10–100 kHz, and preferably about 25 kHZ–2 MHz). This higher frequency may break any cohesive or agglomeration tendencies the drug particulates may have as the drug is dispersed. For drug packages 20 concurrently dispensing drugs from more than one well 40 (such as shown in FIG. 5A) the well can be individually excited with different excitation frequencies.

Figure 3C:
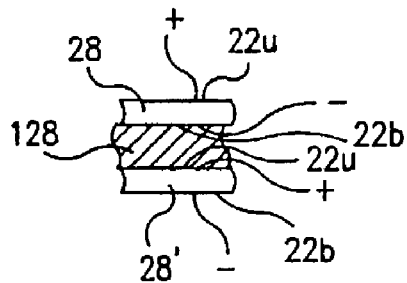
FIG. 3C is a schematic diagram of an alternate embodiment of an individually selectable electric excitation path on a dry powder drug package with multiple piezoelectric substrate layers according to the present invention.

Although the preferred embodiment of the dry powder package 10 is shown and described as employing a single piezoelectric substrate layer 28, other configurations may also be employed. For example, as schematically shown in FIG. 3C, the platform body 20*b* can include two piezoelectric substrate layers 28, 28' separated by an intermediate flexible core 128 with each having the metal trace patterns 22*u*, 22*b*, described above. The core is flexible and concurrently deforms along with the substrate layers 28, 28' in the same direction to oscillate the well of the package. In operation, all of these (four trace patterns) would be concurrently responsive to the application of an electric field in the region of the activated well or receptacle(s) 40. The dual substrate configuration may amplify the mechanical oscillation.

The core 128 can be a neoprene layer with a thin film of adhesive on each side. The piezoelectric substrate layers 28, 28' can then easily be secured to a respective outer surface of the core 128 to sandwich the core 128 therebetween. Preferably, the core 128 is sized to be greater in thickness, and more preferably about an order of magnitude greater in thickness, than the substrate layers 28, 28'. For example, for a substrate layer 28, 28' having a 60 micron width, the core 128 can have a depth or width thickness of about 600 microns.

Figure 3D:
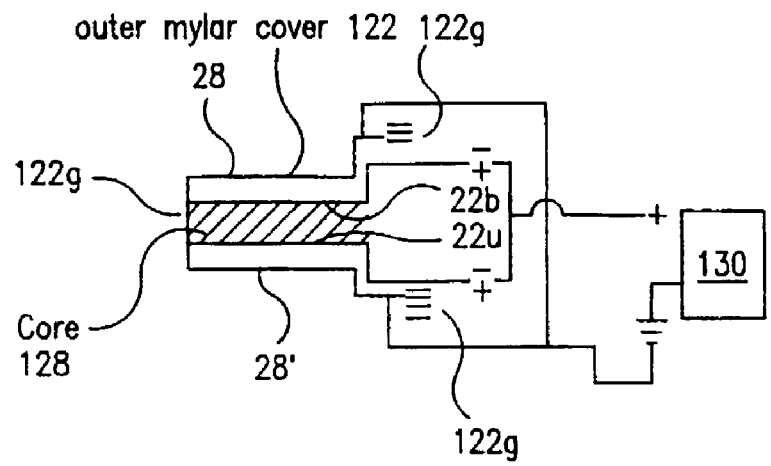
FIG. 3D is a schematic diagram of yet another embodiment of an individually selectable electrical excitation path drug package with multiple piezoelectric substrate layers according to the present invention.

As another alternative, as shown in FIG. 3D, two piezoelectric layers can be used 28, 28' with an intermediate core 128 as above, but each of the substrates 28, 28' may have a single signal metal trace pattern disposed on their internal faces (the faces oriented toward the center core 128). in this embodiment, an external, common ground surface 122g for both the top and the bottom substrate 28, 28'. The external ground surface 122g can be provided on the outer major surfaces of each piezoelectric substrate layer 28, 28' by applying a continuous layer of conductive ink or paint, or by overlaying and enclosing the substrates with a mylar film thereon or other electrical conductive means as is known to those of skill in the art.

As shown in FIG. 3D, for the signal traces 22b (for the top substrate 28) and 22u (for the bottom substrate 28'), the PVDF of each substrate layer 28, 28' is oriented in a manner that the polarity is such that the activation of the single signal trace patterns on each substrate 28, 28' deforms the substrates concurrently in the same direction to oscillate the well of package 20. As shown, the PVDF is arranged onto the core such that each displays a negative to positive polarity, and the trace is applied to the side of the film associated with the positive polarity. The electrical connections can be made by extending the PVDF film a distance on each of the piezoelectric substrate layers 28, 28' separate from the common ground 122g into the controller 125 proximate the control system 100.

In any event, as will be appreciated by those of skill in the art, in order to appreciably "enhance" the piezoelectric effect in the PVDF material, the material is typically exposed to an appropriate electrical poling potential across the thickness of the film for an extended period of time to piezoelectrically "activate" the film.

Preferably, for multiple piezoelectric substrate layer configurations as described above, the core 128 is formed by inserting a neoprene or pliable material core material into a die. The PVDF substrate material layers 28, 28' are preferably introduced onto the core layer 128 such that the desired polarity of the substrate materials are in the proper orientation. For example, the first substrate layer 28 is layered onto the core 128 such that it has a first polarity and the outer layer 60 of the second substrate layer 28' is positioned to contact the core 128 opposing the first outer layer 50 such that it has a second polarity, the second polarity being the reverse of the first polarity (such as shown in FIG. 3D). Alternatively, the substrate layer 28, 28' polarities can have the same orientation, as shown in FIG. 3C.

As demonstrated by the foregoing, in operation, the present invention provides a method of dispersing an inhalable quantity of a dry powder pharmaceutical drug to a patient's airstream, comprising the steps of positioning and holding a DPI having at least one unitized quantity of dry powder pharmaceutical drug in a receptacle portion of a package, the receptacle portion configured with a bottom surface which is operably associated with a piezoelectric polymer; repeatedly applying a voltage differential across the piezoelectric polymer film in the region of the receptacle to deform the receptacle; and expelling the dry powder drug held in the receptacle such that it is dispersed into the airstream or respiratory path of a user during the user's inspiratory inhalation cycle.

Preferably, the deforming step is carried out by flexing the piezoelectric material in the region of the receptacle. Of course, as noted above, the method can also include the steps of measuring the inspiratory air flow rate of a user, and controlling the voltage applied during the applying step responsive to the user's inspiratory flow rate obtained from the measuring step and/or controlling the voltage applied based on a predetermined drug flow property of the drug being dispensed (the latter to be discussed further below).

Another aspect of the present invention is a method of forming a disposable dry powder drug package with active elements thereon. The method includes the steps of configuring a first unitary layer of PVDF film having first and second opposing major surfaces. Electrical traces are formed onto the first and second major surfaces of the PVDF film layer. A plurality of drug wells are formed in the PVDF film proximate the active pad regions. It should be noted that during fabrication of the package, particularly during sterilization procedures, care should be taken to reduce the piezoelectric material's exposure to temperatures above 120° C., particularly after the piezoelectric substrate layer has been activated.

Another aspect of the present invention is control systems for dry powder applications, and particularly for DPI's. As noted above, the fluidization and dispersion of the dry powder drug can be assisted by mechanically oscillating a piezoelectric polymer material incorporated in the drug package. Thus, the excitation path and oscillators are incorporated in the drug packaging (i.e., a disposable multi-dose drug package with active elements). The excitation signals directed to assist in the dispersion of the dry powder can be dependent on flowability characteristics of a particular drug formulation which can be established a priori as will be discussed further below.

Figure 13:
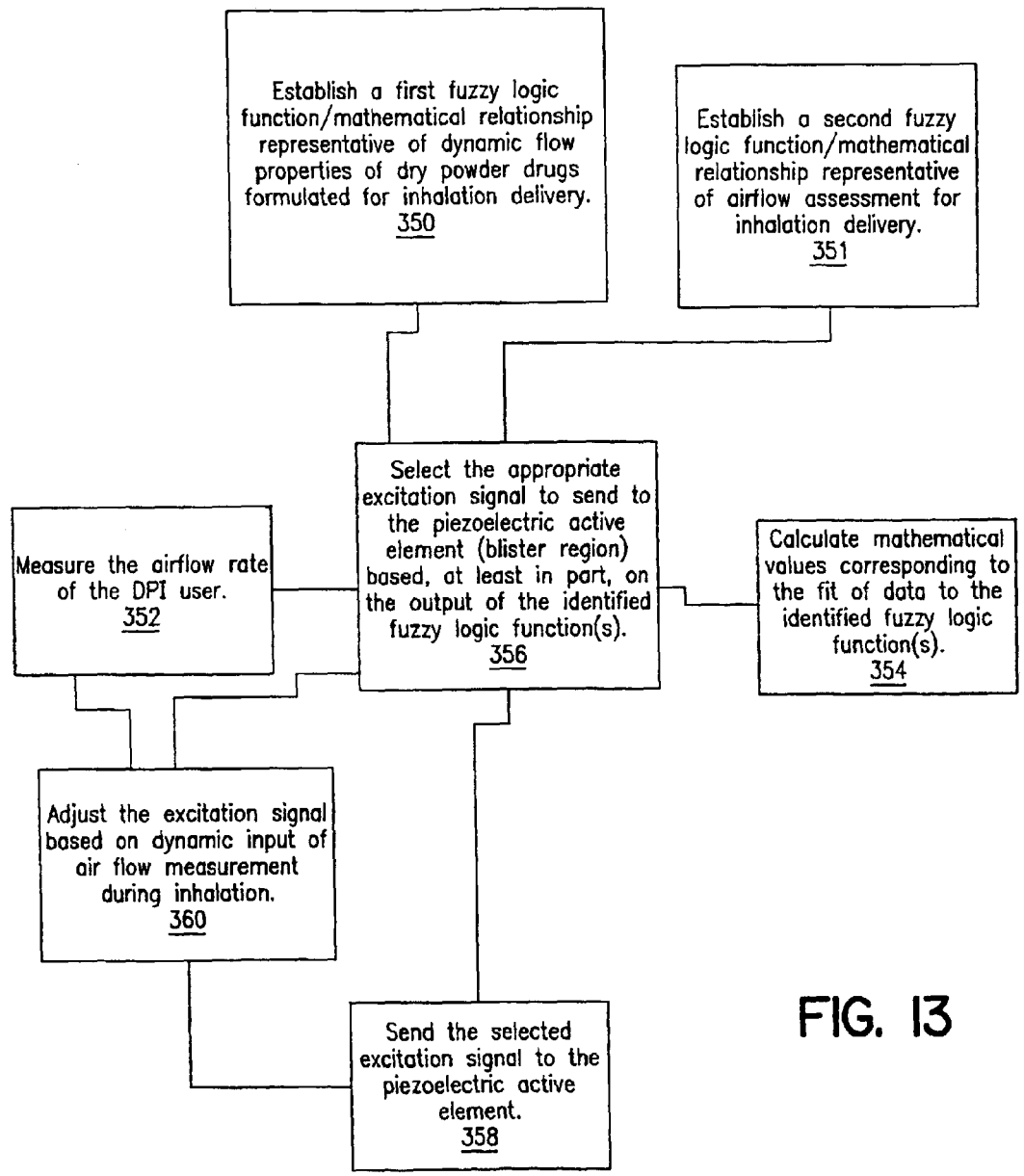
FIG. 13 is a block diagram of a method of controlling the dispersion of a dry powder drug according to the present invention.

The control system preferably employs a "fuzzy logic" analysis methodology which is programmed into the microcontroller. As shown in FIG. 13, a block diagram of one method of controlling the dispersion of a dry powder drug according to the present invention is shown which employs "fuzzy logic". The method preferably includes defining a first fuzzy logic relationship representative or one or more flow properties of the dry powder drug formulated for inhalation (Block 350) and preferably establishing a second fuzzy logic relationship representative of an assessment of good and poor inspiratory airflow desired for administration (Block 351). The method also includes measuring the airflow rate of the user to input into at least one of the fuzzy logic relationships (Block 352). Data (such as density, flowability, etc) associated with the dynamic flow property of the drug being dispersed can be established a prior and loaded into a controller in a computer readable look-up chart. The method can then calculate mathematical values characterizing the fit of the data to the two fuzzy logic relationships (Block 354). For example, analyzing the actual air flow rate of the user in the fuzzy logic flow rate relationship and analyzing the flowability of the powder and excipients being dispersed in the first fuzzy logic relationship.

Still referring to FIG. 13, a desired operating excitation signal based, at least in part, on the characterization of the flowability of the drug formulation as a first fuzzy logic function, and, preferably, the user's airflow rate is also measured (as it relates to his/her inspiratory efforts) and also included (considered) in the fuzzy logic analysis system (either as a part of the first fuzzy logic function or the second fuzzy logic function) to determine the desired operating excitation signal (Block 356). The selected excitation signal is then sent to the selected piezoelectric dispensing element (Block 358). The excitation signal can be adjusted based on dynamic measurement/input of the actual airflow rate of a user (Block 360).

In operation, the controller (programmed with the fuzzy logic analysis methodology) can then analyze the degree of membership associated with the flowability of the drug or the airflow rate of the user to the respective fuzzy logic function (the higher the value the larger the degree of membership to that function). The degree of membership or values of the flowability and/or airflow rate fuzzy logic functions are then related to a to a desired operating signal which is directed to the energy source/delivery system of the drug package to output and actively assist in the dispersion of the dry powder drug. Therefore, the excitation energy or signal output is dependent upon the measured air flow and drug flow characteristics.

The controlled output excitation signal can provide improved dispersions by facilitating fluidization and/or deagglomeration of the dry powder drug during inhalation. The preferred frequencies of the excitation signals are dependent on the powder physiochemical properties and particle size. Thus, the preferred operational excitation signal of the present invention can be selected to be responsive to a particular formulation. That is, the frequencies and subharmonics of the particular formulation can be established, such as described below, and this information can be included in the logic operation to determine the excitation signal to be directed to the piezoelectric polymer element.

The flowability characteristics for the associated "fuzzy logic" functions/parameters associated with the formulations of a plurality of different drugs can be established in a number of ways, such as by analysis of similar drugs having similar particulate sizes, densities, or excipient blends, as well as by actual analysis of the particular formulations. The flowability can be at least partially established by evaluating the powder formulation based on a vibrating spatula analysis. Of course, other analysis techniques can also be employed, such as conventional powder flow analysis via rotating drums. See Crowder et al., *Signal Processing and Analysis Applied to Powder Behavior in a Rotating Drum*, Part. Part. Syst. Charact. 16 (1999) 191–196 (describing Fourier power spectrum of the angle of repose time sequence and the avalanche size variability as a good way to measure a fundamental property of the bulk powder flow). This study also examined lactose excipient blends. This type of analysis can be used to provide flow rankings or input parameter characterizations of powder formulations for the fuzzy logic model.

It is more preferred that measurement of microflow properties of unit dose sized quantities of powders can be employed to rank the flowability of the DPI based control system and provide corresponding input parameters for the fuzzy logic system. See Crowder et al., *An instrument for rapid powder flow measurement and temporal fractal analysis*, 16 Part. Part. Syst. Charact., pp. 32–34 (1999). Using this analysis technique, the flow properties of pharmaceutical excipients were found to be generally fractal in nature. This suggests that small perturbations to the system in the form of subharmonics of the fundamental frequencies of oscillation, (which can be determined by the vibrating spatula technique), can be applied to the control system to drive the powder to a resonance frequency to thereby improve flow or dispersion. See Aranson et al., *Controlled dynamics of interfaces in a vibrated granular layer*, 82 Phys. Ref. Lett. 731–734 (1999).

Measurements of bulk flow and microflow can provide data can be used to establish representative logic and/or to increase the dosing uniformity in the inhaler according to the present invention. It is also preferred that respirable fraction data (typically obtained via a cascade impactor) analysis be included in the flowability and/or energy output fuzzy logic model. A suitable impactor is the Andersen 8-stage non-viable cascade impactor available from a company known as Graseby-Andersen located in Smyrna, Ga.

Preferably, at least one, and preferably both bulk flow and microflow data is considered in modeling the fuzzy logic control system of the present invention. For microflow analysis, a vibrating spatula technique is typically employed using a 60 Hz vibration frequency. See e.g., Crowder et al., *A Semiconductor Strain Gauge Instrument for Rapid Powder Flow Rate Measurement*, 16 Particle and Particle Sys. Charac. pp. 32–34 (1999). As noted in this reference, vibration amplitude was adjustable by a thumbwheel. The adjustment in this analysis was not calibrated, thus amplitudes were not recorded. The resulting fractal dimensions were 1.143+/−0.024 for non-spray dried lactose and 1.001+/−0.001 for the spray dried lactose, and 1.002+/−0.0004 for sieved spray dried lactose. Representative powder bulk flow data and experimental description is discussed in, Crowder et al., *Signal Processing and Analysis Applied to Powder Behavior in a Rotating Drum*, 16 Part. Part. Syst. Charact., pp. 191–196(1999).

It should be also noted that powder flow can also be influenced by ambient conditions, particularly relative humidity. Thus, the control system model may be defined to average the operational conditions across typical conditions. It is anticipated that such an average or a range of typical relative humidities should be sufficient for dispersion purposes, unless the formulation is an especially hygroscopic powder. Of course, adjustments can be programmed for problematic drugs or climates.

Although not required, the control system of the instant invention preferably uses fuzzy logic because the number of variables influencing powder dispersal is very large. Monitoring even a fraction of these variable can be cost-prohibitive as control algorithms derived from system equations relating to the dry powder inhaler and the powder itself can be mathematically difficult and complex. The ability of a control system to accept partial truths or generalities is important where empirically observed effects from a small number of monitored variables are used to provide the basis for dry powder deliveries according to one aspect of the instant invention.

Fuzzy logic is known as a way to express complex relationships. Dr. Lotfi Zadeh of the University of California at Berkeley introduced fuzzy logic in the 1960's. See Zadeh, Lotfi, *Fuzzy Sets, Information and Control*, 8:338–353, 1965. Fuzzy logic is a methodology which generalizes absolute relationships to a continuous form. Unlike conventional classical set theory, where as et of ordered pairs can be defined and membership in the set is absolute, and a computer reads as Boolean truths ("0" or "1"), fuzzy logic represents the results as membership in a function as a substantially continuous series of discrete values of numbers between 0–1 representing degrees of membership or "degrees of truth". Typically, fuzzy logic membership functions do not have simple shapes. Many are "triangles pointing up" and can even be more complex. For example, one author describes a membership function (Tall) for a range of heights which also depends on (a) age, and (c) weight. Thus, whether an individual is tall would depend not only on height, but on the age and weight of the individual. See What is fuzzy logic: www.cs.cmu.edu/Groups/Al/html/fags/ai/fuzzy/part1/fag-doc-2.html. Therefore, data can be aggregated based on a number of partial truths which can then be combined to define a higher truth when certain thresholds are met or exceeded. So, for fuzzy logic models or systems, the degrees of membership in a defined function or can be established which includes a conventional truth table (0 and 1 where 0 is for non-membership and 1 is for complete membership), and values in between to represent intermediate or degrees of membership to the defined function.

Fuzzy logic control systems have been shown to be effective in controlling complex systems. See U.S. Pat. No. 4,319,155, the contents of which are hereby incorporated by references as if recited in full herein.

Figure 15:
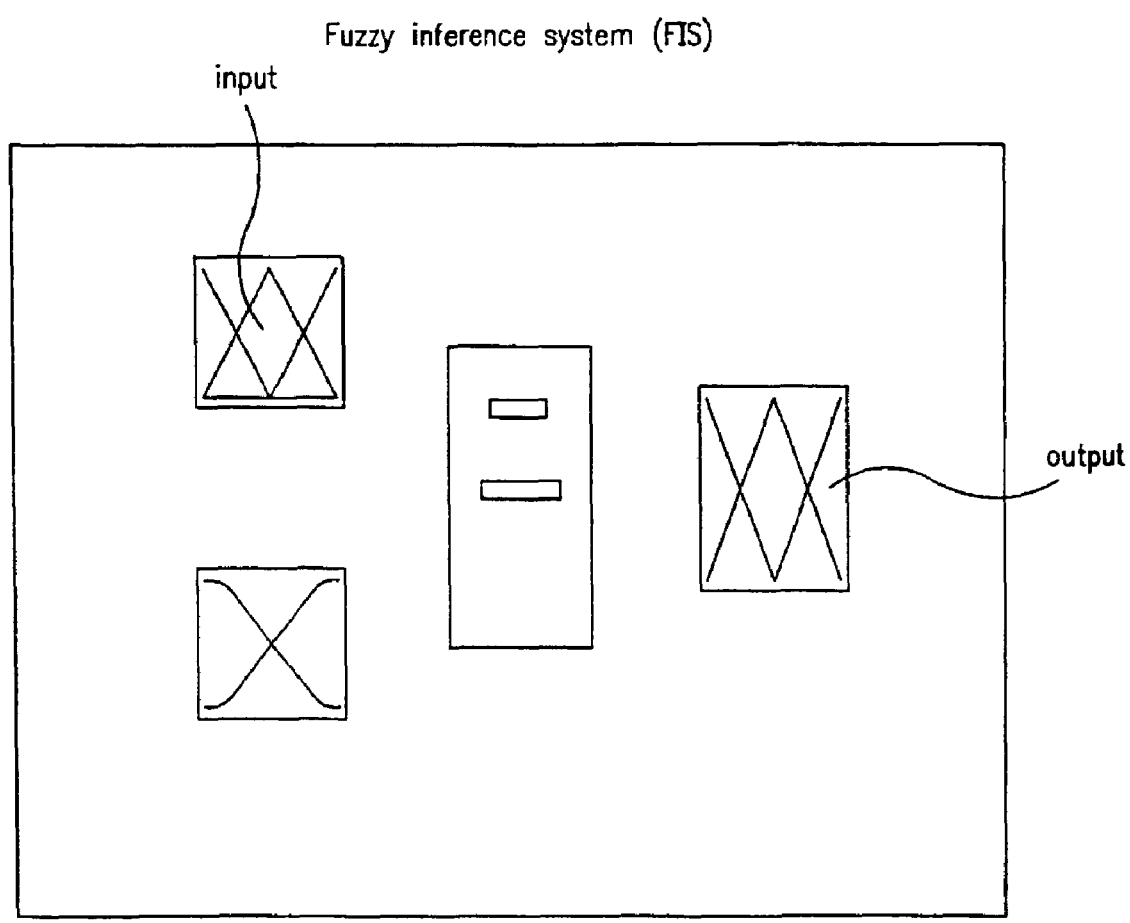
FIG. 15 is a schematic diagram of a fuzzy inference system for determining the degree of membership of selected fuzzy membership functions and adjusting the operation of a DPI according to the present invention.
Figure 17:
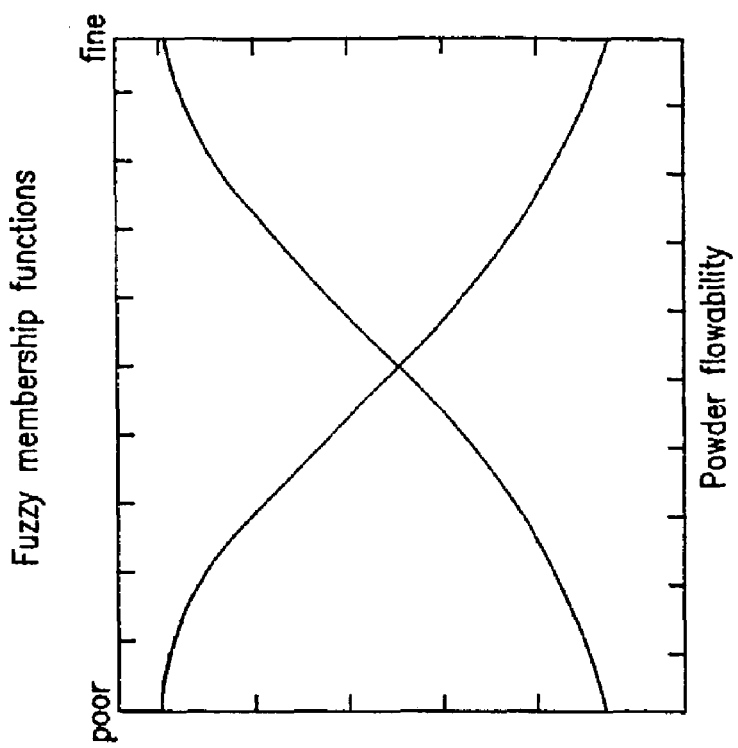
FIG. 17 is a graph of a fuzzy membership function for powder flowability modeling powder flowability of the formulation as poor, good, or otherwise, according to the present invention.
Figure 16:
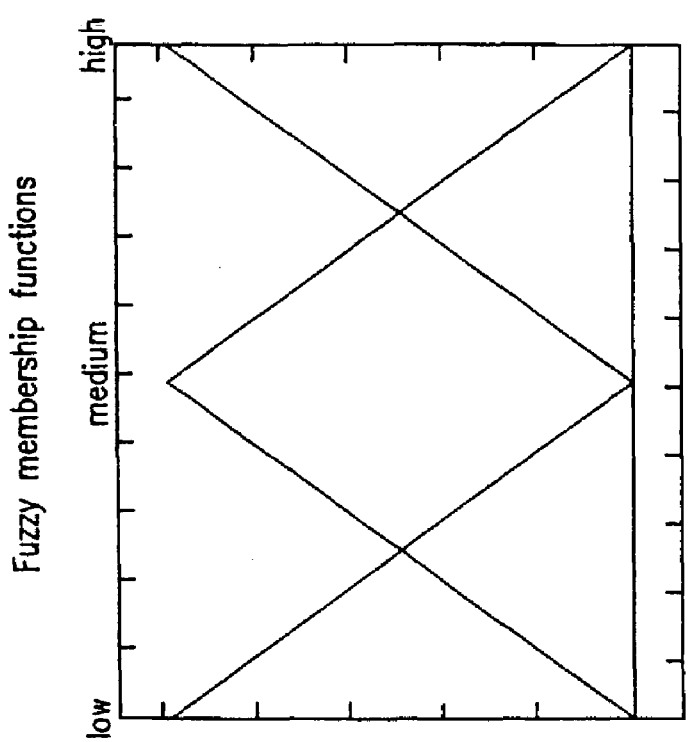
FIG. 16 is a graph of a fuzzy membership function for airflow rate modeling airflow rate as low, medium, and high according to the present invention.

Referring now to FIGS. 15, 16, and 17, preferred fuzzy logic models for dry powder controls systems having a fuzzy inference system and membership functions are graphically shown. As shown, the fuzzy logic system of the instant invention models are selected parameters of powder flowability (FIG. 17) and (inspiratory) airflow rate (FIG. 16). As shown in FIG. 17, the powder flowability rate characterizes the powder along a continuum of values as having poor or good flowability. The identification of poor or good can be based on a plurality of characteristics such as particulate size, density, excipients added thereto, doses, delivery desired (systemic or local), the propensity for agglomeration and the like. Similarly, as shown in FIG. 16, an airflow rate value is fuzzily characterized along the continuum extending from low to high. The airflow function in identifying the airflow rate as high, low, or somewhere in between, can consider a plurality of factors, such as age, size of the inhaler, length of the delivery (inspiratory effort), flow rates of the user, fall off of the inspiratory effort over the delivery time, primary altitude of use, the systemic target, and the like. The data or values of these inputs represent the degree of membership to the respective fuzzy function.

As shown in FIG. 16, the degree of membership values of the flowability variable and the air flow rate variable are then input into another fuzzy logic-based algorithm or function/model which analyzes the data according to preset fuzzy logic rules and determines an appropriate output excitation signal. This fuzzy logic model can define fuzzy logic rules relating desired output energy values/frequencies to a particular drug formulation. An exemplary fuzzy logic output function is stated by the following:

If the powder is cohesive and the flow rate is low, increase the energy input. Preferably, the fuzzy logic control system preferably takes into account (by the fuzzy logic functions used) one or more of the following: the specific drug formulation (such as particulate size, tendency to cohesiveness, etc.), the type of excipient, the geometry of the inhaler, and the inpiratory ability of the user. The fuzzy logic models can bundle multiple parameters together in a manner which is computationally less intensive and less complex over conventional powder flow control systems.

Figure 14:
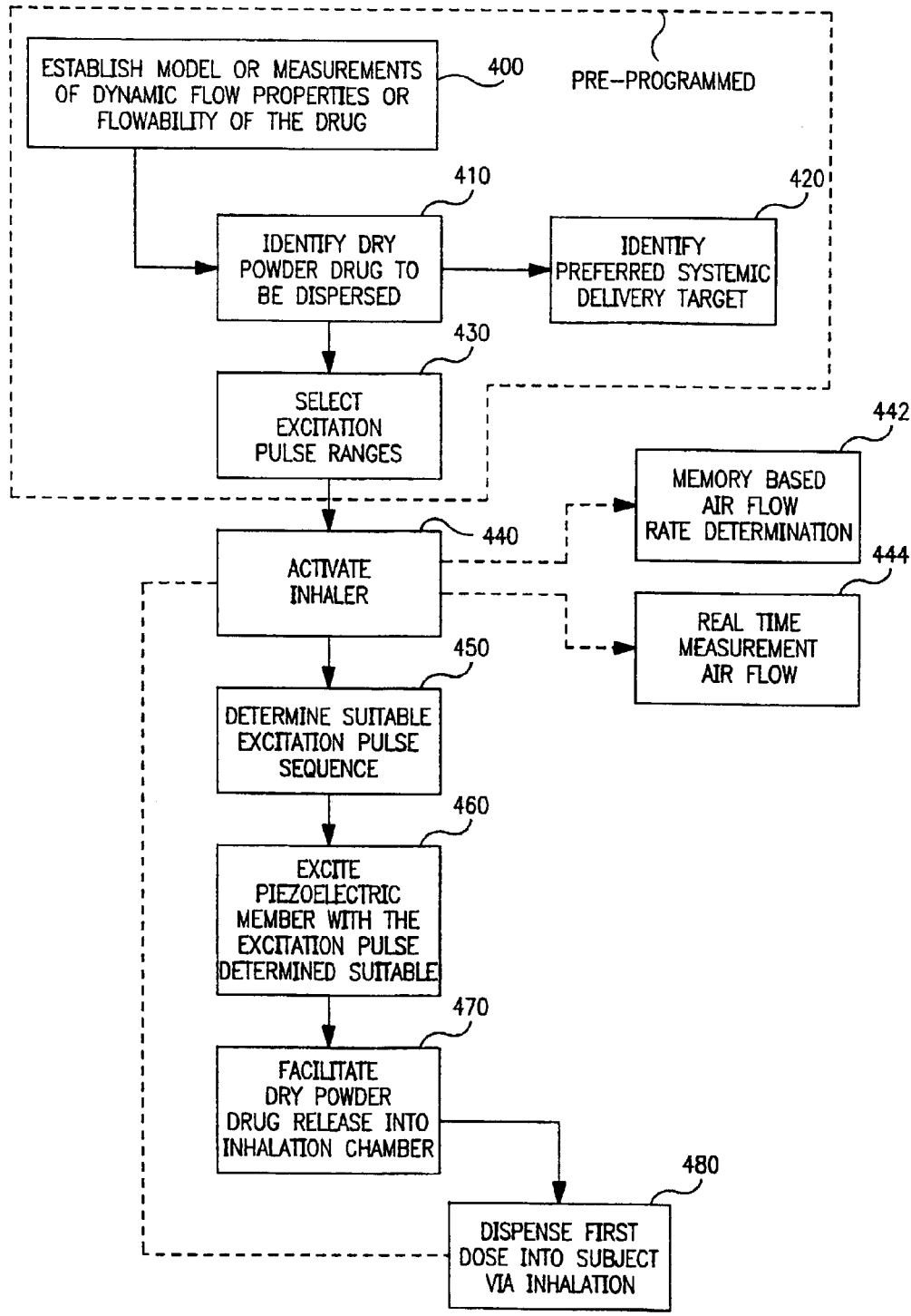
FIG. 14 is a block diagram of a method for controlling the operation of a DPI according to the present invention.

Turning now to FIG. 14, a preferred method of controlling the delivery of a quantity of inhalable dry powder is shown. A model or measurements of the flowability of dry powder drug formulations is established (Block 400). The dry powder drug to be administered or dispersed is identified (Block 410). The preferred systemic delivery target is identified (Block 420). The operational range of selected excitation pulses are identified (Block 430). The steps described in Blocks 400–430 can be pre-programmed such as at a factory site. One or more of the parameters identified in Blocks 400, 410, 420, 430 may be part of a fuzzy logic membership function or functions. During operation, the inhaler is activated (Block 440). A user inspiratory airflow rate can be established and input to the control system of the device. The airflow rate can be a memory-based measurement of the user's capabilities (average or low) (Block 442) or can be a real time measurement proximate to the delivery of the drug (Block 444). A suitable excitation pulse is determined (Block 450). (The determination of the excitation pulse can also be based on a fuzzy logic function which defines airflow rate and flowability as fuzzy variables). The piezoelectric member is excited with the determined excitation pulse (Block 460). The dry powder drug release into the inhalation chamber is facilitated by the excited piezoelectric member (Block 470). A first dose is dispensed into a subject via inhalation (Block 480).

It should be noted that a fuzzy logic model can be defined which can provide information to the physician to assist in the selection of the powder drug and the type of inhaler. For example, for a user with a systemic target A, with an average inspiratory flow rate B, with drug allergies C, using other medications D having potential to reduce the efficacy of a drug, and having other identified risk factors (age, heart disease, diabetes, etc.), the fuzzy logic model can provide the physician with an output which lists suitable inhaler types (geometries), and/or drugs, and/or drug formulations (such as based on ease of flowability, effectiveness).

The control system in the DPI can be preset to operate with a particular drug formulation, or can be programmed to receive a coded (for security) input from a pharmacist or physician based on a UPC or other code associated with the drug to be dispensed. Of course, the DPI may also be configured to electronically read the flowability code based on a computer program readable code means (bar code or memory chip) on the package itself.

It should also be noted that control systems according to the present invention can also be used in dry powder production systems and apparatus. That is, where dry powder substances are dispersed in a manufacturing process, the control system of the instant invention can provide better process controls by the monitoring, feedback, analysis, and adjustment of the operational inputs to the process to provide more reliable and repeatable processes. Typically, the process inputs will be the type of dry powder being employed and its flowability characterization, temperature, humidity, flow rate, etc. Thus, the control systems of the instant invention may be used to facilitate improved conveyor speeds, aperture sizes, feed times, nozzle sizes, and the blending, milling, transport, or capsule filling of pharmaceutical products. In addition, it is anticipated that the concept of using signals specific to powder (and which may be specific to the particular PVDF design) may also be used to convey powder in industrial processes.

The control systems of the instant invention can be used with other active energy dispersion systems such as those described above, including DPI devices with mechanical oscillators and other vibration based systems.

It will be understood that each block of the block diagrams (or block in the flowchart illustrations), and combinations of blocks in the flowchart illustrations (or blocks in block diagram figures), can be implemented by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. The computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks and/or block diagrams.

Accordingly, blocks of the block diagrams or in a flowchart illustration support combinations of means for performing the specified functions and program instruction means for performing the specified functions. It will also be understood that each block of the block diagram or flowchart illustrations, and combinations of blocks in the block diagrams or flowchart illustrations, can be implemented by special purpose hardware-based computer systems which perform the specified functions or steps, or combinations of special purpose hardware and computer instructions.

EXAMPLE

An experimental embodiment of a DPI employing a piezoelectric excitation element for vibrating the powder during dispersion employs a design wherein the polymer membrane vibratory element has an associated capacitance "C" of about 1800 pf. The capacitance value corresponds to the size i.e., area (and thus shape) of the blister or vibratory element. The transformer used to step up the 5 Vp-p input voltage is presently exhibiting an inductance of about 23 mH on the secondary side. The transformer is used to step up the voltage to a 150 Vp-p excitation voltage to the blister. Thus together, the transformer and piezoelectric element define an amplifier which can be described as having a resonant frequency expressed by the equation:

$$f=1/(2\pi(LC)^{1/2})$$

where "L" is the inductance of the transformer and C is the capacitance of the polymer membrane vibratory element. This yields a calculated resonant frequency for the experimental embodiment of about 25 kHz. The resonant frequency determined experimentally was 24 kHz. At this frequency, the output measured at about 7 mm from the front of the speaker was 72.4 db. Powder was placed on the active element and the movement of the powder was observed. The maximal displacement of the powder as determined by observation occurred at about 31 kHz. Thus, the 31 kHz frequency was chosen for experimental evaluations.

In order to obtain higher resonant frequencies, the transformer and/or the piezoelectric polymer element can be reconfigured. The capacitance of the polymer is about 250 picofarads/cm$^2$. Preferred piezoelectric elements can be configured to exhibit capacitances of from about 1000–2000 picofarads, and more preferably about 1500 picofarads. Stated differently, the size of the blister is preferably such that it has an area which is from about 4–8 cm$^2$, and more preferably about 6 cm$^2$. This means for a circular blister, at least an approximately 1 to 1.5 centimeter radius blister can be employed.

A new active element has been constructed with a smaller area to reduce the capacitance of the circuit and thereby allow for use of higher frequency signals.

Advantageously, recent results comparing the fine particle fraction (FPF) of particles emitted from the device when a signal was input to the active element against that with no signal indicates that a much larger percentage of FPF is obtained with the piezoelectric active element. The FPF can be considered to be that part of the aerosol which, in use, would be substantially delivered to the lungs. The experimental determination of the FPF was conducted using an 8 stage Andersen non-viable cascade impactor. For a 31 kHz signal amplitude modulated at 60 Hz, the FPF emitted was 0.11=/-0.0002 (n=4). With no signal, the FPF was 0.05=/-0.0003 (n=4). Thus comparatively speaking, about twice the amount of FPF was generated with the PVDF element. Using a one tailed test, it was determined that the FPF was increased by the use of a signal with p<0.05. It is anticipated that a baffle located in the airstream can cause a larger fraction of the powder to be emitted from the device.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included herein.

That which is claimed is:

1. A method of controlling the active delivery of a dry powder drug in an inhaler configured with an active energy assisted drug dispersion system, comprising the steps of:
   establishing a priori a flowability characterization of a plurality of dry powder drug formulations;
   measuring the airflow rate of a user using the dry powder inhaler;
   determining a degree of membership of the flowability of the drug to be dispersed utilizing a first fuzzy logic function;
   determining a degree of membership of the measured airflow rate of the user with a second fuzzy logic function; and
   controlling an excitation signal directed to the active energy system of the inhaler based on the determined degrees of membership.

2. A method according to claim 1, wherein the steps of controlling comprises determining a degree of membership with a third fuzzy logic function, the degree of membership associated with the values associated with the determined degrees of membership to the first and second fuzzy logic functions.

3. A method according to claim 1, wherein the first fuzzy logic function associated with the flowability of the drug analyzes the propensity for the drug to be cohesive, and wherein the second fuzzy logic function associated with the measured inspiratory airflow rate of a user using the dry powder inhaler determines the degree of membership based on a dynamically measured airflow rate of a user.

4. A dry powder inhaler having an active energy assisted dispersing system, comprising:
a housing configured to receive a multi-dose dry powder package therein, said housing having an airstream exit flow path;
a control system positioned in said housing, said control system comprising:
a controller;
a power source operably associated with said controller;
a transformer operably associated with said controller and said power source configured to generate excitation energy directed to a selected region of the multi-dose dry powder package; and
computer readable program code programmed in said controller to determine the excitation energy directed to the multi-dose dry powder package.

5. A dry powder inhaler having an active energy assisted dispersing system according to claim 4, further comprising an air flow sensor positioned in said exit flow path, said air flow sensor operably associated with said controller, and wherein said computer readable program code further comprises computer code which considers the measured airflow rate to determine the excitation energy directed the dry powder package.

6. A dry powder inhaler having an active energy assisted dispersing system according to claim 5, further comprising computer readable computer program code which establishes a fuzzy logic model of the flowability of the dry powder formulation being administered and an associated suitable excitation energy, and wherein said computer readable computer program code which determines the excitation energy considers the results of the fuzzy logic flowability model to determine the excitation energy directed the dry powder package.

7. A dry powder inhaler having an active energy assisted dispersing system according to claim 4, further comprising a disposable multi-dose dry powder package having a plurality of spatially separated dry powder drug doses held thereon, said package including a piezoelectric polymer film substrate and a plurality of spatially separate electrical signal paths thereon, said dry powder package positioned in said housing such that said excitation signal is directed to a selected one of said plurality of signal paths to thereby deliver an excitation signal to cause the package to oscillate in the vicinity of the drug dose held in the selected signal path to actively disperse said dry powder into said exit flow path.

8. A dry powder inhaler according to claim 4, wherein said exit flow path is configured with an irregular shaped exit flow path to thereby facilitate turbulence is the air as it travels through said exit flow path.

9. A dry powder inhaler according to claim 8, wherein said air flow path has a width, and wherein said irregular shaped flow path comprises a baffle which is attached to said housing such that it extends a distance across the width of said air flow path.

10. A dry powder inhaler having an energy assisted dispersing system, comprising:

a housing configured to receive a dry powder package with at least one meted dose of dry powder, said housing having an airstream exit flow path;

a control system positioned in said housing configured to generate at least one operational excitation output signal having a plurality of associated frequencies, the operational excitation output signal comprising frequencies derived from an a priori flow analysis of the dry powder in the dry powder package, the frequencies being dependent on physiochemical properties and particle size of the dry powder; and a power source operably associated with said control system.

11. A dry powder inhaler according to claim 10, wherein the computer readable program code configured with the at least one operational excitation output signal comprises computer readable program code with a look-up table of a range of operational excitation output pulses having associated frequencies, amplitudes and signal patterns associated therewith, each excitation output signal corresponding to a predetermined type of dry powder formulation.

12. A dry powder inhaler according to claim 10, the control system comprising a controller with computer readable program code configured to initiate the excitation output signal and further comprising computer readable computer program code for selecting the excitation output signal responsive to the dry powder package selected for inhalation.

13. A dry powder inhaler according to claim 10, further comprising a piezoelectric polymer member in the housing in communication with the control system, wherein, in operation, the control system is configured to transmit the excitation output signal to the piezoelectric polymer member to rapidly flex the piezoelectric member to thereby vibrate the dry powder during inhalation.

14. A dry powder inhaler according to claim 13, wherein the drug package is a multi-dose blister drug package with a plurality of spaced apart blisters, wherein the piezoelectric polymer member defines a portion of each blister, and wherein the control system is configured to transmit the excitation output signal to the piezoelectric polymer member associated with at least one blister during an inhalation.

15. A dry powder inhaler according to claim 13, wherein the piezoelectric polymer film is PVDF.

16. A dry powder inhaler according to claim 14, wherein the dry powder package holds a plurality of spaced apart blisters, at least pairs of blisters holding different dry powders, and wherein the control system is configured to transmit different excitation output signals to the at least pairs of blisters to dispense each of the different dry powders during an inhalation.

17. A dry powder inhaler having an energy assisted dispersing system, comprising:

a housing configured to receive a disposable dry powder package with at least one meted dose of dry powder, said housing having an airstream exit flow path;

a piezoelectric polymer member disposed in the housing configured to communicate with dry powder during an active inhalation cycle to vibrate the dry powder in the exit flow path; and a control system positioned in said housing, said control system comprising:

a controller comprising computer program code configured to generate at least one operational excitation output signal having associated fundamental and subharmonic frequencies dependent on flow properties and particle size of the dry powder being dispensed during the active inhalation cycle; and a power source operably associated with said control system.

18. A dry powder inhaler according to claim 17, wherein the computer readable program code configured with the at least one operational excitation output signal comprises computer readable program code with a look-up table of a range of operational excitation output pulses having associated frequencies, amplitudes and signal patterns associated therewith, each excitation output signal corresponding to a predetermined type of dry powder formulation.

19. A dry powder inhaler according to claim 17, the controller further comprising computer readable computer program code for selecting the excitation output signal responsive to the dry powder package selected for inhalation.

20. A dry powder inhaler according to claim 17, wherein the drug package is a multi-dose blister drug package with a plurality of spaced apart blisters, wherein the piezoelectric polymer member defines a portion of each blister, and wherein the control system is configured to transmit the excitation output signal to the piezoelectric polymer member associated with at least one blister during an inhalation.

21. A dry powder inhaler according to claim 17, wherein the piezoelectric polymer film is PVDF.

22. A method of actively assisting dispersion of a dry powder during inhalation using an inhaler, comprising:

transmitting an operational excitation output signal having a plurality of frequencies that are derived from a flow analysis of the dry powder in the inhaler to vibrate the dry powder during inhalation, the excitation signal frequencies being dependent on physiochemical properties and particle size of the dry powder; and vibrating the dry powder held in an inhaler responsive to the transmitting step during inhalation.

23. A method according to claim 22, wherein the excitation signal frequencies comprise harmonic and subharmonic flow characteristic frequencies derived from the flow analysis of the inhalable dry powder.

24. A method according to claim 23, wherein the inhaler is configured to hold two different dry powders apart from each other before inhalation in the inhaler, and wherein the transmitting and vibrating steps are carried out to concurrently disperse both dry powders together to a user during inhalation, and wherein the harmonic and subharmonic flow characteristic frequencies are related to the physiochemical properties and particle sizes of the two different dry powders.

25. A new method according to claim 22, wherein the transmitting step transmits the excitation signal to a piezoelectric polymer member that comprises thin film PVDF with conductive portions.

26. A new method according to claim 22, wherein the transmitting and vibrating steps rapidly flex a piezoelectric polymer member generally upward and downward with the dry powder residing thereabove during at least a portion of an active inhalation cycle.

27. A dry powder inhaler having an energy assisted dispersing system, comprising:

a housing configured to receive at least one meted dose of dry powder, said housing having an airstream exit flow path;

a vibration system positioned in said housing configured to generate at least one excitation output signal comprising a plurality of dry powder-specific selected frequencies associated with physiochemical properties and particle size of the dry powder in the housing, wherein, in operation during inhalation, the vibration system is configured to apply the plurality of selected dry powder frequencies generally concurrently to the dry powder to disperse the dry powder to a user; and a power source held by the housing operably associated with said vibration system.

28. A dry powder inhaler according to claim 27, wherein the selected frequencies are derived from an a priori flow analysis of the dry powder.

29. A dry powder inhaler according to claim 27, wherein the selected frequencies comprise at least one of the following flow characteristic frequencies of the dry powder: (a) fundamental harmonic and (b) subharmonic frequencies.

30. A dry powder inhaler according to claim 28, wherein the selected frequencies are derived from a rotational drum flow analysis of the dry powder.

31. A dry powder inhaler according to claim 27, further comprising a dry powder containment system that releasably holds a plurality of different dry powders separate from each other for generally concurrent dispensing of the different dry powders.

32. A dry powder inhaler according to claim 31, wherein the vibration system is configured to generate the excitation signal using selected frequencies derived from individual flow analysis of the different dry powders.

33. A dry powder inhaler according to claim 32, wherein the vibration system comprises a piezoelectric polymer in communication with the different dry powders during active inhalation.

* * * * *